United States Patent
Deisher

(10) Patent No.: US 9,962,408 B2
(45) Date of Patent: May 8, 2018

(54) COMPOSITIONS AND METHODS TO INHIBIT STEM CELL AND PROGENITOR CELL BINDING TO LYMPHOID TISSUE AND FOR REGENERATING GERMINAL CENTERS IN LYMPHATIC TISSUES

(71) Applicant: Ave Maria Biotechnology LLC, Seattle, WA (US)

(72) Inventor: Theresa Deisher, Seattle, WA (US)

(73) Assignee: AVM Biotechnology LLC, Seattle, WA (US)

( * ) Notice: Subject to any disclaimer, the term of this patent is extended or adjusted under 35 U.S.C. 154(b) by 0 days. days.

(21) Appl. No.: 15/410,759

(22) Filed: Jan. 19, 2017

(65) Prior Publication Data

US 2017/0128493 A1    May 11, 2017

Related U.S. Application Data

(63) Continuation of application No. 13/212,916, filed on Aug. 18, 2011, now abandoned.

(60) Provisional application No. 61/374,943, filed on Aug. 18, 2010, provisional application No. 61/441,485, filed on Feb. 10, 2011, provisional application No. 61/449,372, filed on Mar. 4, 2011.

(51) Int. Cl.
| | | |
|---|---|---|
| *A01N 63/00* | (2006.01) |
| *A61K 31/00* | (2006.01) |
| *C12N 5/00* | (2006.01) |
| *A61K 35/28* | (2015.01) |
| *A61K 31/573* | (2006.01) |
| *C07K 16/28* | (2006.01) |
| *A61K 39/395* | (2006.01) |
| *A61K 39/00* | (2006.01) |
| *A61K 35/12* | (2015.01) |
| *C12N 5/071* | (2010.01) |

(52) U.S. Cl.
CPC ............ *A61K 35/28* (2013.01); *A61K 31/573* (2013.01); *A61K 39/3955* (2013.01); *C07K 16/2878* (2013.01); *A61K 35/12* (2013.01); *A61K 2039/505* (2013.01); *C12N 5/0602* (2013.01)

(58) Field of Classification Search
CPC ...... A61K 31/573; A61K 35/12; A61K 35/28; C12N 5/0602
USPC .............................. 435/375; 424/93.7; 514/1
See application file for complete search history.

(56) References Cited

PUBLICATIONS

Kolf et al., 2007, Arthritis Research & Therapy, vol. 9, p. 204, 10 pages.*
Alenzi et al., 2011, African Journal of Biotechnology, vol. 10(86), pp. 19929-19940.*
Wu et al., 2012, Aging Research reviews, vol. 11, p. 32-40.*
Steinert et al., 2007, Arthritis Research & therapy, vol. 9, No. 3, 213, p. 1-15.*
Li et al., 2009, Transplant Immunology, vol. 21, p. 70-74.*
Sprangers et al., 2008, Kidney International, vol. 74, p. 14-21.*

* cited by examiner

*Primary Examiner* — Shin Lin Chen
(74) *Attorney, Agent, or Firm* — Baumgartner Patent Law; Marc Baumgartner

(57) ABSTRACT

The present invention relates to compositions and methods of inhibiting stem cell binding to organs and tissues, including the blocking of stem cell binding to germinal centers present in lymph tissue. Disclosed are compositions and methods for regenerating germinal centers in lymphatic tissue. Included in the compositions are adjuvants, agonists to CD40, CD28 and the IL-21 receptor, and antagonist to CD20.

15 Claims, 1 Drawing Sheet

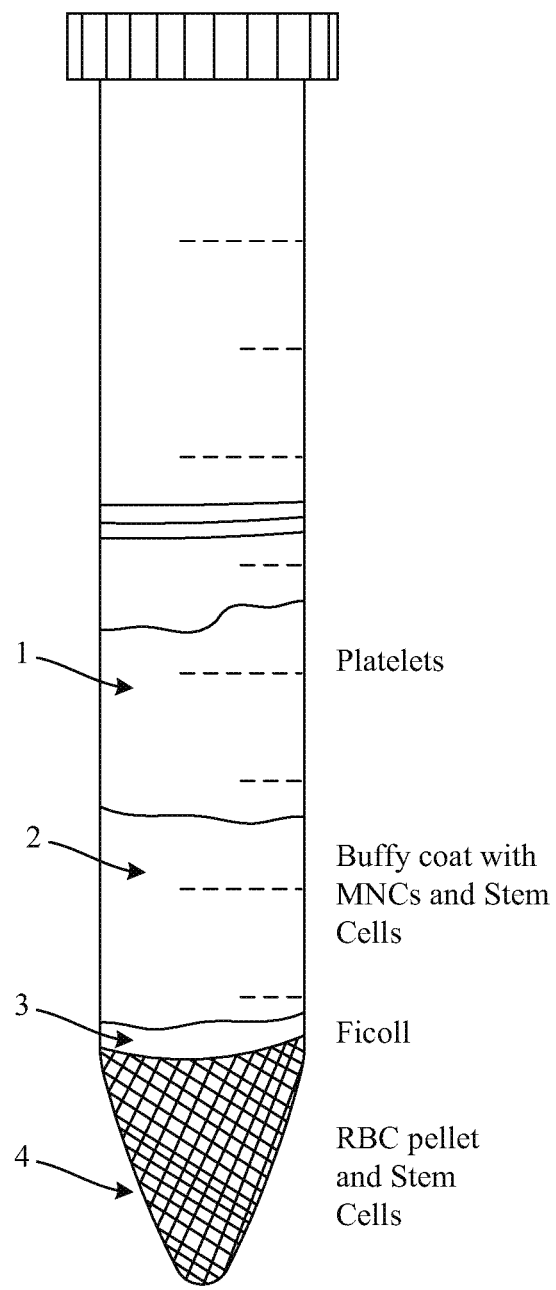
Layers resulting from gradient centrifugation of whole blood

COMPOSITIONS AND METHODS TO INHIBIT STEM CELL AND PROGENITOR CELL BINDING TO LYMPHOID TISSUE AND FOR REGENERATING GERMINAL CENTERS IN LYMPHATIC TISSUES

CROSS-REFERENCE TO RELATED APPLICATIONS

This application is a continuation of U.S. patent application Ser. No. 13/212,916, filed Aug. 18, 2011, which claims benefit of priority to U.S. Provisional Application No. 61/374,943 filed Aug. 18, 2010; and to U.S. Provisional Application No. 61/441,485 filed Feb. 10, 2011; and to U.S. Provisional Application No. 61/449,372 filed Mar. 4, 2011. All of the foregoing applications are hereby incorporated by reference in their entirety.

FIELD OF THE INVENTION

Subject matter of the disclosure concerns methods and compositions to modulate stem cell binding to organs and tissues and for regenerating germinal centers in lymphatic tissues.

BACKGROUND OF THE INVENTION

Regenerative Medicine is the process of creating living, functional tissues to repair or replace tissue or organ function lost due to damage, or congenital defects. This field holds the promise of regenerating damaged tissues and organs in the body by stimulating previously irreparable organs to heal themselves.

One method used to regenerate tissue or organ function is the delivery of stem cells to the affected organ or tissue. However, stem cells are not well retained in the organ targeted for tissue regeneration even when the stem cells are directly injected into the tissue of the injured organ. Imaging studies in humans and animals have demonstrated that most of the delivered stem cells can be found within the spleen within an hour after stem cell injection. Animal studies have also demonstrated that surgical removal of the spleen prior to stem cell therapy after induced myocardial infarction improved functional recovery of the damaged hearts (Blood, Vol 84, No 5: 1482-1491, 1994; NATURE 410:701-705, 2001). Splenectomy has also been shown to improve engraftment in human patients after bone marrow transplantation (Stem Cells Dev 13(1):51-62, 2004; Transplant Proc. 28(2):736-7, 1996; Am J Hematol. 22(3):275-83, 1986). However, splenectomy is also associated with surgical mortality, sepsis, and lifelong thrombotic complications (Blood Rev. 14(3):121-129, 2000; Leukemia. 15(3):465-467, 2001; Pediatr Transplant 13(2): 171-176, 2009)

Thus, there is a need to develop methods and compositions that can be used to prevent localization of stem cells in the spleen and other lymphoid tissues without removal of the spleen.

DESCRIPTION OF THE INVENTION

Overview

The present invention fills this need by providing for methods and compositions for inhibiting binding of stem cells to lymphoid tissue comprising administering stem cells to an individual in conjunction with a therapeutic agent or agents that inhibit binding of stem cells to lymphoid tissue, in particular to germinal centers in lymph nodes and germinal centers in the spleen. The term 'in conjunction with' means together, before or after the stem cell treatment. 'Stem cell treatment' means the act of administering stem cells to the individual, mobilizing stem cells from within the individual's endogenous stem cell stores, or relying on spontaneous release of stem cells from the individual's endogenous stem cell stores.

For example, patients treated with stem cells to elicit organ regeneration have demonstrated reductions in mortality and improvements in function following stem cell therapy, although the stem cell treatments do not generally restore the patient to their functional status prior to organ injury. Reductions in stem cell binding to the spleen and other lymphatics augment the numbers of circulating stem cells that can be attracted to the injured organ and thereby augment the degree of functional recovery induced by steal cell treatment of that patient.

In administering the therapeutic agents that inhibit the binding of stem cells to lymphatic tissues it is preferred to administer the therapeutic agents 1-14 days prior to treatment, more preferably 3-7 days and most preferably 3-4 days prior to treatment with stem cells or mobilization of stem cells. In administering the therapeutic agents that inhibit the binding of stem cells to lymphatic tissues in conjunction with spontaneously released stem cells from the individual's endogenous stem cell stores it is preferred to administer the therapeutic agents over a period of 1-60 days, more preferably 1-30 days, and most preferably 1-14 days.

Agents that inhibit the binding of stem cells to lymphoid tissues, particularly to the germinal centers of lymphoid tissues, include radiation, chemotherapeutic agents, immune suppressants and antagonists to CD45 and antagonists to CD26. Stem cells found within the mononuclear fractions from whole blood or bone marrow, or purified stem cells from whole blood or bone marrow, bind to the white pulp regions in the spleen, more specifically to germinal centers in the white pulp of lymphatic tissue including the spleen, and even more specifically to active germinal centers in the white pulp of the spleen. Antibodies to CD45, particularly to the epitope identified by the 30-F11 rat IgG2b anti-mouse anti-CD45 monoclonal antibody, reduce stem cell binding to the identified sites in the spleen, making more stem cells available for biodistribution to the targeted injured organ, and enhancing tissue regeneration and functional recovery.

In another embodiment of the present invention therapeutic agents are administered that reduce, destroy or ablate active germinal centers in the lymphoid tissue thus resulting in the reduction of the binding of stem cells to the lymph tissue. Another embodiment of the present invention describes methods to reduce the number of active germinal centers in the spleen to reduce stem cell binding to the spleen, thereby increasing the numbers of circulating stem cells available for delivery or homing to damaged organs in need of repair. Agents that suppress the immune response may reduce the numbers of active germinal centers in the spleen and other lymphatic tissues. General categories of immune modulators include agents that interfere with the synthesis of purines, the anti-metabolites, radiation, radiation to the spleen, immunosuppressants, glucocorticoids, anti-beta amyloid agents, anti-rhesus factor, anti-TNF agents, anti-eotaxins, anti-T cell receptor (TCR) agents, anti-interferons agents, anti-interferon alpha agents, anti-interferon beta agents, anti-interferon gamma agents, anti-TGF agents, anti-TGFalpha agents, anti-TGF beta agents, anti-Integrins agents, anti-alpha 4 agents, anti-Interleukin agents, anti-Interleukin 1 agents, anti-interleukin 2 agents, anti-Interleukin 4 agents, anti-Interleukin 5 agents, anti-interleukin 6 agents, anti-Interleukin 12 agents, anti-Interleukin 13 agents, anti-Interleukin 23 agents, anti-IgE agents, anti-Vascular Adhesion Protein (VAP) agents, anti-B7 agents, anti-Vascular Endothelial Growth Factor (VEGF) agents, anti-BAFF (BLyS) agents, anti-CTLA4 agents, anti-complement agents, anti-CD2 agents, anti-CD3 agents, anti-CD4 agents, anti-CD5 agents. anti-CD20 agents, anti-CD23 agents, anti-CD25a agents, anti-CD40 agents, anti-CD 154 (CD40L) agents, anti-CD62L agents, anti-CD80 agents, anti-CD 147 agents, anti-LFA1 agents, anti-(CD11a) agents, anti-CD18 agents, inhibitors of purine synthesis, inhibitors of pyrimidine synthesis, anti-proliferative agents, anti-metabolite agents, anti-folate agents, and anti-mTOR agents.

Adenosine deaminases deficiency will also lead to reduced active germinal center formation as will agents which trigger the accumulation of deoxyATP (J Immunol 171: 5562-5570, 2003). Similarly, agents that enhance the expression of or activate CCR7 will lead to diminished active germinal center formation.

Chemotherapeutic agents can also be used to inhibit the formation of the germinal centers of lymphoid tissue or to destroy or ablate the germinal centers. Representative examples include alkylating agents, anti-metabolites, plant alkaloids, topoisomerase inhibitors, antineoplastics and arsenic trioxide.

Examples of alkylating agents include cisplatin and carboplatin, as well as oxaliplatin, are alkylating agents. They impair cell function by forming covalent bonds with the amino, carboxyl, sulfhydryl, and phosphate groups in biologically important molecules.

Examples of antimetabolites azathioprine, mercaptopurine, capecitabinefluorouracil—which become the building blocks of DNA. They prevent these substances from becoming incorporated in to DNA during the "S" phase (of the cell cycle), stopping normal development and division. They also affect RNA synthesis. Due to their efficiency, these drugs are the most widely used cytostatics.

Alkaloids include the vinca alkaloids and taxanes. Vinca alkaloids include vincristin, vinblastin, vinorelbine, and vindesine. Taxanes include taxol, paclitaxel and docetaxel.

Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide.

Antineoplastic agents include dactinomycin, doxorubicin, epirubicin, and bleomycin.

Definitions

Definitions used to describe the embodiments of the invention:

The term agonist as used herein means any entity that activates a specific receptor or downstream signaling pathway essential to mediate the receptor's effect(s). Agonists may include but are not limited to antibodies, antibody fragments, soluble ligands, small molecules, cyclic peptides, cross-linking agents.

The term antagonist as used herein means any entity that interferes with the binding of a receptor's counter structure(s), or with the activation of a specific receptor or downstream signaling pathway essential to mediate the receptor's effect(s). Antagonists may include but are not limited to antibodies, antibody fragments, soluble ligands, Fc fusion receptors, chimeric receptors, small molecules, cyclic peptides, peptides.

The term inhibitor as used herein means any entity that diminishes the target effect of a specific ligand or its receptor. Inhibitors may be small molecules, antisense agents, nucleic acids including siRNA and microRNA.

SUMMARY OF THE INVENTION

Lymphatic Tissue, Lymph Nodes, Spleen and Germinal Centers

Lymphatic Tissue is a specialized form of reticular connective tissue in the lymphatic system that contains large numbers of lymphocytes. This tissue type makes up the spleen, the thymus, and the tonsils, as well as visceral nodes, peyer's patches and lacteals that are ail associated with mucous membranes of the gastro-intestinal tract.

A lymph node is a small ball-shaped organ of the immune system, distributed widely throughout the body including the armpit and stomach/gut and linked by lymphatic vessels. Lymph nodes are garrisons of B-cells, T-cells, and either immune cells. Lymph nodes are found all through the body, and act as filters or traps for foreign particles. The lymph node is surrounded by a fibrous capsule, and inside the lymph node the fibrous capsule extends to form trabeculae. The substance of the lymph node is divided into the outer cortex and the inner medulla surrounded by the former ail around except for at the hilum, where the medulla comes in direct contact with the surface. The outer cortex consists mainly of the B cells arranged as follicles, which may develop a germinal center when challenged with an antigen, and the deeper cortex mainly consisting of the T cells. There is a zone known as the subcortical zone where T-cells (or cells that are mainly red) mainly interact with dendritic cells, and where the reticular network is dense.

The spleen is an intraperitoneal organ located on the left side of the abdomen between the stomach and the diaphragm. This organ is a major regulatory site of the immune system. It is a vascular organ, having a large arterial blood supply. On entering the spleen, the blood flow enters a meshwork of dilated blood vessels, or "sinuses", which lie between large masses of lymphocytes. The walls of the sinuses contain phagocytes that are capable of engulfing dead cells and foreign particles in the blood and removing them from the general circulation. Like the lymph nodes, the spleen is an important source of antibodies, however, to a greater extent than the lymph nodes, the spleen is concerned with the removal of abnormal or normally worn out ("dying") red blood cells from the circulation by destroying them.

The spleen contains both a white pulp and a red pulp. The red pulp of the spleen holds macrophages that normally filter and remove senescent or defective red blood cells (RBCs) and antibody-coated bacteria or red blood cells from the circulation. The white pulp of the spleen contains the lymphoid compartments and is crucial for immune surveillance and response: it synthesizes antibodies against invading pathogens and releases platelets and neutrophils in response to bleeding or infection. During development the spleen is believed to have multiple roles including being the first site of hematopoiesis (at six weeks of gestation). While it was long believed that the spleen loses its hematopoietic function during the early stages of development when bone marrow hematopoiesis takes over, recent research has identified the adult spleen as a site of stem cell generation, stem cell differentiation into different lineages and stem cell storage (Trends Mol Med 11(6):271-276, 2005;) However, the sites within the spleen where exogenous stem cells accumulate and the molecular mechanisms by which exogenous stem cells bind to the spleen are not known.

The periarterial lymphoid sheaths (PALS) of the white pulp of the spleen are populated mainly by T cells, while the lymphoid portions are populated mainly by B cells. Germinal centers (GC) are sites within lymph nodes or lymph nodules in peripheral lymph tissues, and in the white pulp of the spleen where intense mature B lymphocytes, otherwise known as Centrocytes rapidly proliferate, differentiate, mutate through somatic hypermutation and class switch during antibody responses. Germinal centers are an important part of the B-cell humoral immune response. They develop dynamically after the activation of B-cells by T-dependent antigen. Histologically, the GCs describe microscopically distinguishable parts in lymphoid tissues. Activated B-cells migrate from the primary focus into the primary follicles follicular system and begin monoclonal expansion in the environment of follicular dendritic cells (FDC).

After several days of expansion the B cells mutate their antibody-encoding DNA and thus generate a diversity of clones in the germinal center. This involves random substitutions, deletions and insertions due to somatic hypermutation. Upon some unidentified stimulus from the FDC, the maturing B cells (Centroblasts) migrate from the dark zone to the light zone and start to expose their antibody to their surface and in this stage are referred to as Centrocytes. The Centrocytes are in a state of activated apoptosis and compete for survival signals from FDCs that present the antigen. This rescue process is believed to be dependent on the affinity of the antibody to the antigen. The functional B-cells have then to interact with helper T cells to get final differentiation signals. This also involves isotype switching for example from IgM to IgG. The interaction with T cells is believed to prevent the generation of autoreactive antibodies. The B cells become either a plasma cell spreading antibodies or a memory B cell that will be activated in subsequent contacts with the same antigen. They may also restart the whole process of proliferation, mutation and selection according to the recycling hypothesis.

The B cells contained within the white pulp region of the spleen can be further divided into specific areas, identified by staining with specific molecular markers. The marginal zone of the spleen contains noncirculating mature B cells that border on the white pulp creating a separation between the white and the red pulp and express high levels of CD23 and IgM and CD24 and CD79a, and measurable levels of CD9 and CD22. The mantle zone surrounds normal germinal center follicles and expresses CD21, CD23 and CD38. The follicular zone is contained within the germinal centers and expresses high levels of IgD and CD23, intermediate levels of CD21 and CD24, and can also be identified by PNA staining. The germinal center is best distinguished by PNA binding and expresses higher levels of CD54 than the follicular zone. Germinal centers have a special population of helper T cells that seem to distribute evenly in ail germinal centers. Germinal centers are traditionally associated with immune responses that require T helper cells, although this is not absolute. Germinal centers are where hypervariable gene mutation occurs and high affinity IgG producing B cells are generated. Active germinal centers have tangible macrophages and CD21 expressing dendritic cells. Follicular centers can also be identified by the expression of CD45R (B220) [Toxicologic Pathology, 35:366-375, 2007). CD45R follicular centers are found surrounding germinal centers expressing Bc16 and Bc12. BioEssays 29:166-177, 2007; Toxicol Pathol 34(5): 648-655, (2006)]

CD45 is a common leukocyte antigen also known as PTPRC (protein tyrosine phosphatase, receptor type C), found on all differentiated hematopoietic cells except erythrocytes and plasma cells. It is also expressed in lymphomas, B-cell chronic lymphocytic leukemia, hairy cell leukemia, and acute non-lymphocytic leukemia. It has shown to be essential in B- and T-cell antigen receptor signaling. The CD45 family consists of multiple members that are all products of a single complex gene. This gene contains 34 exons and three exons of the primary transcripts are alternatively spliced to generate up to eight different mature mRNAs and after translation eight different protein products. These three exons generate the RA, RB and RC isoforms.

Various isoforms of the CD45 antigen exists. The CD45 antigen isoforms include CD45RA, CD45RB, CD45RC, CD45RAB, CD45RAC, CD45RBC, CD45RO, CD45R (ABC). CD45A is located on naive T cells and CD45RO is located on memory T cells. CD45 is also highly glycosylated. CD45R is the longest protein and migrates at 200 kDa when isolated from T cells. B cells also express CD45R with heavier glycosylation, bringing the molecular weight to 220 kDa, hence the name B220; B cell isoform of 220 kDa. B220 expression is not restricted to B cells and can also be expressed on activated T cells, on a subset of dendritic cells and other antigen presenting cells. Naive T lymphocytes express large CD45 isoforms and are usually positive for CD45RA. Activated and memory T lymphocytes express the shortest CD45 isoform, CD45RO, which lacks RA, RB and RC exons. This shortest isoform facilitates T cell activation. The cytoplasmic domain of CD45 is one of the largest known and it has an intrinsic phosphatase activity that removes an inhibitory phosphate group on a tyrosine kinase called Lck (in T cells) or Lyn/Fyn/Lck (in B cells) and activates it. CD45 can exist in both monomeric and dimeric forms, and dimerization may downregulate CD45 phosphatase activity (Blood v 103(9):3440-3447, 2004).

As CD45 is expressed on all hematopoietic cells and is the most broadly expressed of all hematopoietic antigens, it has been used to isolate the population of cells that also contains hematopoietic stem cells in transplant and other models of stem cell reconstitution, however, mesenchymal stem cells, while derived from a population of CD45+ earlier precursors, are generally found to be CD45 negative (Stem Cells 28:140-151, 2010). A complete absence of all isoforms of CD45 has been demonstrated in mice to influence stem cell retention, motility and homing to the bone marrow and to play a role in the generation of functional B cells in the spleen from earlier stem cells (J. Exp. Med. 205:2381-2395, 2008). Interestingly, CD45 knock-out mice, lacking all isoforms of CD45, had reduced numbers of cKit+Lin-hematopoietic progenitor cells in the bone marrow, but increased numbers within the spleen.

30-F11 is a rat monoclonal IgG2b raised against thymus and spleen of mouse origin. Clone 30-F11 reacts to both alloantigens (CD45.1 and CD45.2) and all isoforms of CD45, 30-F11 and clone 30-F4 each block binding by the other to CD45, indicating that they bind to the same or overlapping epitopes on CD45 (J Immunol 127(3):982-986, 1981). Likewise, both of these clones cross-block with an antibody described by Dennert et. al., however, the anti-CD45 antibody 55-6.1 does not cross-block with either 30-F11 or 30-F4 (Cell Immunol 53:350-364, 1980).

Radiolabeled 30-F11 antibody shows highest accumulation in mouse spleen (60%), with only 20% accumulation in marrow (Blood 93(2):737-745, 1999), and has been used in mice to deliver targeted hematopoietic irradiation. The 30-F11 antibody has been used to identify, in conjunction with Sca1 antigen, stem cell fractions from the muscle of mice, since CD45 is expressed on all hematopoietic cells (PNAS 99 1341-1346, 2002). Radiolabeled 30-F11 and f(ab)'2 fragments of the 30-F11 have been evaluated as a method to deliver radiotherapy. 30-F11 uptake was most dramatic in the spleens of mice, followed by axillary lymph node (Cancer Res 52(5):1228-34, 1992).

The CD45 polypeptide can be produced by published procedures. Methods for preparing anti-CD45 polyclonal and monoclonal antibodies are well known in the art (see for example, Sambrook et al., Molecular Cloning: A Laboratory Manual, Second Edition (Cold Spring Harbor, N.Y., 1989); and Hurrell, J. G. R., Ed., Monoclonal Hybridoma Antibodies: Techniques and Applications (CRC Press, Inc., Boca Raton, Fla., 1982), which are incorporated herein by reference). As would be evident to one of ordinary skill in the art, polyclonal antibodies can be generated from a variety of warm-blooded animals such as horses, cows, goats, sheep, dogs, chickens, rabbits, mice, and rats. Production of humanized antibodies is well known. See Riechmann L. Clark M, Waldmann H, Winter G (1988). "Reshaping human antibodies for therapy". Nature 332 (6162): 332:323. Queen C, Schneider W P, Selick H E, Payne P W, Landolfi N F, Duncan J F, Avdalovic N M, Levitt M, Junghans R P, Waldmann T A (December 1989). "A humanized antibody that binds to the interleukin 2 receptor.". Proc Natl Acad Sci USA. 86 (24): 10029-33. Norderhaug L, Olafsen T. Michaelsen T E, Sandlie I. (May 1997). "Versatile vectors for transient and stable expression of recombinant antibody molecules in mammalian cells.". J Immunol Methods 204 (1): 77-87.

Methods and Agents to Prevent Stem Cell Binding to Lymphatic Tissue

Other particular embodiments provide for a method to moderate stem cell binding to a spleen by exposing the spleen to a solution of antagonists to a cluster of differentiation 45 (CD45) antigen. The solution of antagonist to the CD45 antigen may be configured or formulated to bind to the 30-F11 epitope. The solution of antagonists to the CD45 antigen may be formulated to promote therapeutic regeneration by enhancing stem cell delivery to the damaged tissues or organs. The solution containing the antibody to the CD45 antigen may be formulated to bind to the 30-F11 epitope and to a human equivalent of the 30E-11 epitope.

The present invention describes methods to reduce stem cell binding to lymphatic tissue such as the lymph nodes and the spleen, and uses of these methods to treat human patients. The invention describes the specific site within the spleen where circulating stem cells bind in the spleen, and methods to increase or decrease stem cell binding to this site. Immunoflourescent and histological analysis of fresh thick spleen sections demonstrated that stem cells circulating in the vasculature bind to active germinal centers in the spleen when administered either in vivo or ex vivo, as shown in example 1, 2, 3, and 4. One method to decrease the amount of stem cell binding to the spleen is to deliver agents that block binding of the administered stem cells to the molecular target on the active germinal centers of the spleen. According to the process of the present invention, antibody 30-F11 binds to mouse CD45 antigen and blocks stem cell binding to germinal centers of the mouse spleen. Anti-human anti-CD45 antibodies that may be the equivalent to the 30-F11 rat IgG2b anti-mouse CD45 include YAML568 which recognizes epitope P of human CD45 (J Nucl Med 47:1335-1341, 2006; In: Leucocyte Typing III: White Cell Differentiation Antigens pp 811-814, 1987; Transplantation 40:538-544, 1985), anti-CD45 clone HI30, or YTH-24 and YTH-54 anti-human anti-CD45 antibodies.

Another embodiment of the present invention is the use of antagonists to CD26 such as antibodies to CD26 to inhibit stem cell binding to germinal centers. As CD26 is expressed by stem cells and is the antigen present on stem cells that adheres to lymph tissue in particular to germinal centers in the lymph tissue. By blocking the CD26 on stem cells, the stem cells are unable to bind to lymph tissues.

Agents that Inhibit, Down-Regulate the Formation of Germinal Centers or Destroy or Ablate Germinal Centers Another embodiment of the present invention is to inhibit stem cell binding to the lymph tissues by inhibiting or down-regulating the proliferation of the germinal centers or to destroy or ablate the germinal centers. Germinal centers (GCs) develop dynamically after the activation of B-cells by T-dependent antigen. The T-Cell antigen that activates the B-cells and thus induces proliferation of the germinal centers is CD40L (also known as CD154) that binds to the CD40 receptor present on the B-cells. This binding of the CD40L to the CD40 receptor not only activates the B-cells but also induces proliferation of the germinal centers. Thus, another embodiment of the present invention is comprised of administering to an individual an agent that inhibits the binding of CD40L to CD40. Examples of such agents are antagonistic antibodies to CD40 or to CD40L.

Another protein important for the development of germinal centers is the 'signaling lymphocyte activation molecule-associated protein' (SAP). (Hai Qui, et al., Nature, 455:764-769 (2008). Thus, an antibody against SAP would inhibit the formation of germinal centers and thus inhibit binding of stem cells to lymph tissues.

IL-21 is another polypeptide important for germinal center B cell differentiation and proliferation through a B cell-intrinsic mechanism. The absence of IL-21 signaling profoundly affects the B cell response to protein antigen, reducing splenic and bone marrow plasma cell formation and GC persistence and function, influencing their proliferation, transition into memory B cells, and affinity maturation. [Zotos, D., et al, JEM 207:365-378 (2010)]. Thus by administering antagonists such as antibodies to IL-21 to someone the germinal centers can be down-regulated and their formation inhibited. This would inhibit the binding of stem cells to the lymph tissue and spleen due to the lack of germinal centers in the lymph tissue.

Chemotherapeutic agents can inhibit binding of stem cells to germinal centers of lymphoid tissues including lymph nodes, Peyer's patches, and the white pulp of the spleen. Also, agents that suppress the immune response may reduce the numbers of active germinal centers in the spleen. Such agents include:

Azathioprine, (IMURAN®, Prometheus Laboratories, San Diego, Calif.) administered in 3-5 mg/kg, daily, preferably 3-4 days prior to the administration of the stem cells. Azathioprine interferes with the synthesis of purines (adenine and guanine), which is required for DNA synthesis. Fast-growing cells, including T-cells and B-cells, are particularly affected by the inhibition of purine synthesis.

Corticosteroids such as dexamethasone, prednisolone, methylprednisolone, dexamethasone sodium phosphate and betamethsaone. Dexamethasone tablets (Merck) and Dexamethasone sodium phosphate injections can be given 1-14 days prior to treatment with stem cells more preferably 3-7 days and most preferably 3-4 days prior to treatment with stem cells. The total amount of dexamethasone that is administered is an amount sufficient to down-regulate the germinal centers in the lymphatic tissue so that stem cells cannot bind to the lymph tissue. The total amount of dexamethasone over the period of time can range from 2 mg to 3 g, preferably 27 mg in total. The daily dose of dexamethasone can range from 0.75 mg to 700 mg per day preferably 7 mg per day. Dexamethasone, like the other glucocorticoid steroids inhibits the formation and proliferation of germinal centers in the lymph tissues.

Mycophenolic acid (Myfortic® delayed release capsules, Novartis Pharmaceuticals Corporation East Hanover, N.J., 720 mg administered twice daily (1440 mg total daily dose) on an empty stomach, one hour before or two hours after food intake), preferably 3-4 days prior to administration of stem cells. (CellCept® Roche Labs, Nutley, N.J., mycophenolate mofetil) Tablets and Capsule, Oral Suspension, mycopbenolate mofetil hydrochloride) for Injection Intravenous, the 2-morpholinoethyl ester of mycophenolic acid (MPA), administered IV 1 g twice a day orally 1.5 g administered twice a day, preferably 3-4 days prior to the administration of the stem cells. It inhibits inosine monophosphate dehydrogenase, the enzyme that controls the rate of synthesis of guanine monophosphate in the de novo pathway of purine synthesis used in the proliferation of B and T lymphocytes. Mycophenolate is potent and can be used in place of the older anti-proliferative azathioprine. It is usually used as part of a three-compound regimen of immunosuppressants, also including a calcineurin inhibitor (ciclosporin or tacrolimus) and prednisolone.

Leflunomide, Sanofi-Aventis U.S. LLC, Bridgewater, N.J. 100 mg per day for three days, 3-4 days prior to administration of the stem cells. Leflunomide is a pyrimidine synthesis inhibitor belonging to the DMARD (disease-modifying antirheumatic drug) class of drugs, which are chemically and pharmacologically very heterogeneous. Leflunomide is an immunomodulatory drug inhibiting dihydroorotate dehydrogenase (an enzyme involved in de novo pyrimidine synthesis) (abbreviation DHODH).

Teriflunomide, the active metabolite of leflunomide, Sanofi-Aventis U.S. LLC, Bridgewater, N.J. 100 mg per day for three days, preferably 3-4 days prior to the administration of the stem cells, Methotrexate—is an antimetabolite and antifolate drug. It acts by inhibiting the metabolism of folic acid. It is administered orally or intramuscularly in doses of 15 to 30 mg daily for up to five days, preferably 3-4 days prior to the administration of the stem cells. Mylan Pharmaceuticals. Morgantown, W. Va.

Immunosuppresant Macrolides:

Tacrolimus reduces interleukin-2 (IL-2) production by T-cells. in capsule or injection forms, 0.10-0.15 mg/kg/day, preferably 3-4 days prior to the administration of the stem cells. (Astellas Pharma US, Inc. Deerfield, Ill.).

Ciclosporine—Ciclosporin is thought to bind to the cytosolic protein cyclophilin (immunophilin) of immunocompetent lymphocytes, especially T-lymphocytes. Marketed as Sandimmune®, in the form of capsules, oral solution or injection, and dosed at 14-18 mg/kg/day, preferably 3-4 days prior to the administration of the stem cells. (Novartis Pharmaceuticals Corporation, East Hanover, N.J.).

Pimecrolimus (Elidel) is an ascomycin macrolactam derivative. It has been shown in vitro that pimecrolimus binds to macrophilin-12 and inhibits calcineurin. Thus pimecrolimus inhibits T-cell activation by inhibiting the synthesis and release of cytokines from T-cells. Pimecrolimus also prevents the release of inflammatory cytokines and mediators from mast cells. Pimecrolimus is used as a topical 1% cream for up to 6 weeks, preferably prior to the stem cell therapy.

Gusperimus is a derivative of the antitumor antibiotic spergualin, and inhibits the interleukin-2-stimulated maturation of T cells to the S and G2/M phases and the polarization of the T cells into IFN-gamma-secreting Th1 effector T cells, resulting in the inhibition of growth of activated naive CD4 T cells. It is administered SC, 0.5 mg/kg/day for consecutive 21 days, preferably completed 3-4 days prior to the administration of the stem cells. Nippon Kayaku Co., Ltd.

Everolimus (RAD-001), administered orally at a dose of 10 mg/day, preferably 3-4 days prior to the administration of the stem cells. Novartis, East Hanover, N.J., under the tradenames Zortress (USA).

Thalidomide Thalidomide may reduce the levels of TNF.alpha., (THALOMID®, Celgene Corporation, Summit, N.J.). Acceptable dosing is 100-300 mg/day preferably at bedtime 1 hour after evening meal, preferably 3-4 days prior to the administration of the stem cells.

Lenalidomide is a derivative of thalidomide 50,000 times more potent than thalidomide in inhibiting tumor necrosis factor-alpha, and has less severe adverse drug reactions. Celgene Corporation, Summit, N.J.) 25 mg once daily orally on Days 1-21, preferably 3-4 days prior to the administration of the stem cells.

Anakinra is a recombinant, non-glycosylated version of human IL-1RA (RA for receptor antagonist) Kineret® Biovitrum, Stockholm, Sweden delivered as injection concentrate containing 100 mg each single dose, within 7-14 days and preferably 3-4 days prior to the administration of the stem cells.

Infliximab (trade name REMICADE®) is a monoclonal antibody against tumour necrosis factor alpha (TNF.alpha.). Centocor Ortho Biotech, Horsham, Pa. administered by intravenous infusion at a dose of from 3 mg/kg up to 10 mg/kg, within 7-14 days and preferably 3-4 days prior to the administration of the stem cells.

Golimumab (CNTO 148) is a human monoclonal antibody and is marketed under the brand name Simponi. Golimumab targets TNF-alpha. Centocor Ortho Biotech, Horsham, Pa., administered by as a subcutaneous injection of 50 mgs in 0.5 mls within 7-14 days and preferably 3-4 days prior to the administration of the stem cells.

Adalimumab (HUMIRA, Abbott Laboratories, North Chicago, Ill.) is a TNF inhibitor, adalimumab binds to TNF.alpha., preventing it from activating TNF receptors; adalimumab was constructed from a fully human monoclonal antibody, marketed in both preloaded 0.8 mL syringes and also in preloaded pen devices each containing 40 mg of adalimumab. To down-regulate the germinal centers prior to stem cell administration of at least 40 mg of adalimumab should be administered within 7-14 days and preferably 3-7 days prior to stem cell administration. Preferably two 40 mg-doses of adalimumab should be administered within 7-14 days and preferably 3-7 days prior to administration of the stem cells.

Certolizumab pegol is a monoclonal antibody directed against tumor necrosis factor alpha. More precisely, it is a PEGylated Fab' fragment of a humanized TNF inhibitor monoclonal antibody. It is administered as two subcutaneous injections of 200 mg, injections, within 7-14 days and preferably 3-4 days prior to the administration of the stem cells. (UCB Inc., Atlanta, Ga.).

Temsirolimus (Pfizer Corp.) is a specific inhibitor of mTOR (mammalian target of rapamycin) and interferes with the synthesis of proteins that regulate proliferation, growth, and survival of tumor cells. The recommended dose of temsirolimus is 25 mg IV infused over 30-60 minutes, within 7-14 days and preferably within 3-4 days prior to the administration of the stem cells.

Zotarolimus is a semi-synthetic derivative of rapamycin, Abbot Laboratories, North Chicago, Ill.)

Biolimus A9 Biosensors International, Singapore

Eculizumab (trade name Soliris) is a monoclonal antibody directed against the complement protein C5. This antibody blocks the cleavage of C5 and halts the process of complement-mediated cell destruction. Soliris is administered as an IV infusion administered in 600-mg doses or 900-mg doses, within 7-14 days and preferably 3-4 days prior to the administration of the stem cells. (Alexion Pharmaceuticals Cheshire, Conn.)

Mepolizumab (proposed trade name Bosatria) is a humanized monoclonal antibody that recognizes interleukin-5 (IL-5) administered in as an infusions of 750 mg, within 7-14 days and preferably 3-4 days prior to the administration of the stem cells. GlaxoSmithKline, King of Prussia, Pa.

Omalizumab (trade name Xolair, Genentech/Novartis) is a humanized antibody Omalizumab is a recombinant DNA-derived humanized IgG1k monoclonal antibody that selectively binds to human immunoglobulin E (IgE). Xolair (Omalizumab) 150 to 375 mg is administered SC, within 7-14 days and preferably 3-4 days prior to the administration of the stem cells.

Nerelimomab (BAYX) is a mouse anti-TNF antibody, and can be administered at 10 mg/kg within 7-14 days and preferably 3-4 days prior to the administration of the stem cells.

Faralimomab is a mouse anti-TNF antibody, and can be administered at 10 mg/kg within 7-14 days and preferably 3-4 days prior to the administration of the stem cells.

Elsilimomab (also known as B-E8) is a mouse monoclonal antibody and an immunosuppressive drug. According to the present invention, it can be administered at a dose of 10 mg/kg within 7-14 days and preferably 3-4 days prior to administration of stem cells.

Lebrikizumab is a humanized monoclonal antibody that is designed to bind specifically to EL-13 and can be administered at 10 mg/kg within 7-14 days and preferably 3-4 days prior to the administration of the stem cells. Genentech, South San Francisco, Calif.

Ustekinumab (experimental name CNTO 1275, proprietary commercial name Stelara, Centocor) is a human monoclonal antibody. It is directed against interleukin 12 and interleukin 23, naturally occurring proteins that regulate the immune system and immune-mediated inflammatory disorders. 2 injections, one-month apart, of either 90 or 45 milligrams, or a single 45 mg injection, completed within 7-14 days and preferably 3-4 days prior to administration of stem cells.

Muromonab-CD3 (trade name Orthoclone OKT3, marketed by Janssen-Cilag) is a monoclonal antibody targeted at the CD3 receptor, a membrane protein on the surface of T cells. It is administered 5 mg/day in a single bolus intravenous injection for 10 to 14 days. The administration should be completed within 7-14 days and preferably 3-4 days prior to the administration of the stem cells. Children weighing less than 30 lb should receive 2.5 mg/day (Ortho Biotech, Raritan, N.J.)

Otelixizumab is a monoclonal antibody that targets the epsilon chain of CD3. It is administered 5 mg/day in a single bolus intravenous injection for 10 to 14 days. The administration should be completed preferably within 7-14 days and 3-4 days prior to the administration of the stem cells. Children weighing less than 30 lb should receive 2.5 mg/day. The antibody is being developed by Tolerx, Inc. in collaboration with GlaxoSmithKline and is being manufactured by Abbott Laboratories.

Teplizumab is a humanized Fc-engineered monoclonal antibody also known as MGA031 and hQKT3.gamma.1 (Ala-Ala). It is an anti-CD3 antibody. It can be administered according to the present invention at a dose of 5 mg/day in a single bolus intravenous injection for 10 to 14 days. The administration should be completed within 7-14 days and preferably 3-4 days prior to the administration of the stem cells. Children weighing less than 30 lb should receive 2.5 mg/day (Eli Lilly. Indianapolis, Ind.

Visilizumab (tentative trade name Nuvion, PDL BioPharma Inc.) is a humanized monoclonal antibody that targets CD3 on activated T-Cells. It can be administered according to the present invention at a dose of 5 mg/day in a single bolus intravenous injection for 10 to 14 days. The administration should be completed within 7-14 days and preferably 3-4 days prior to the administration of the stem cells. Children weighing less than 30 lb should receive 2.5 mg/day.

Cleноliximab is a monoclonal antibody against CD4. It can be administered according to the present invention at a dose of 5 mg/day in a single bolus intravenous injection for 10 to 14 days. The administration should be completed within 7-14 days and preferably 3-4 days prior to the administration of the stem cells.

Keliximab is a monoclonal antibody that binds to white blood cells via the protein CD4. It is administered at a dose of 3 mg/kg infusion within 7-14 days and preferably 3-4 days prior to the administration of the stem cells.

Zanolimumab (expected trade name HuMax-CD4) is a human monoclonal antibody that targets CD4 and is administered at a dose 20 mg/kg/day within 7-14 days and preferably 3-4 days prior to the administration of the stem cells. (Genmab, A/S COPENHAGEN/TenX Biopharma, Inc., Philadelphia, Pa.).

Efalizumab (trade name Raptiva, Genentech, Merck Serono) is a recombinant humanized monoclonal antibody. Efalizumab binds to the CD11a subunit of lymphocyte function-associated antigen 1. According to the present invention, it can be administered once weekly by subcutaneous injection at a dose of 20 mg/kg, within 7-14 days and preferably 3-4 days prior to the administration of the stem cells.

Erlizumab, also known as rhuMAb, is a recombinant humanized monoclonal antibody developed by Genentech under a partnership with Roche. According to the present invention, it can be administered once weekly by subcutaneous injection at a dose of 20 mg/kg, within 7-14 days and preferably 3-4 days prior to the administration of the stem cells. The drug works by blocking a growth factor in blood vessels. Specifically, erlizumab targets CD18 and an LFA-1 integrin.

Afutuzumab is an anti-CD20 monoclonal antibody. According to the present invention, it can be administered once weekly by subcutaneous injection at a dose of 20 mg/kg, within 7-14 days and preferably 3-4 days prior to the administration of the stem cells. (Hoffmann-La Roche Inc.)

Ocrelizumab is a humanized anti-CD20 monoclonal antibody. It targets mature B lymphocytes. It is under development by Hoffmann-La Roche's subsidiary Genentech, and Biogen Idec. According to the present invention, it is dosed at 200 mg & 600 mg within 7-14 days and preferably 3-4 days prior to the administration of the stem cells.

Pascolizumab is an anti-IL-4 humanized monoclonal antibody. According to the present invention, it can be administered once weekly by subcutaneous injection at a dose of 20 mg/kg, within 7-14 days and preferably 3-4 days prior to the administration of the stem cells.

Lumiliximab is a monoclonal antibody that targets CD23. According to the present invention, it can be dosed at 50 mg/m2, to 450 mg/m2, to 500 mg/m2 within 7-14 days and preferably 3-4 days prior to the administration of the stem cells. The drug is a chimeric antibody from *Macaca irus* and *Homo sapiens*. (Biogen IDEC)

Teneliximab is a chimeric monoclonal antibody binding to the immune stimulatory protein CD40. According to the present invention, it can be administered once weekly by subcutaneous injection at a dose of 20 mg/kg, within 7-14 days and preferably 3-4 days prior to the administration of the stem cells.

Toralizumab (IDEC 131) is a humanized monoclonal antibody. According to the present invention, it can be administered once weekly by subcutaneous injection at a dose of 20 mg/kg, within 7-14 days and preferably 3-4 days prior to the administration of the stem cells. (IDEC Pharmaceuticals Corporation)

Aselizumab is an anti-CD62L administered by I.V. infusion at doses ranging from 0.5-mg/kg, 1.0-mg/kg, and 2.0-mg/kg within 7-14 days and preferably 3-4 days prior to the administration of the stem cells.

Galiximab is an anti-CD80 (Biogen Idec) monoclonal antibody administered at a dose of 500 mg/m2 IV within 7-14 days and preferably 3-4 days prior to the administration of the stem cells. It is a chimeric antibody from *Macaca irus* and *Homo sapiens*

Gavilimomab is a mouse monoclonal antibody (also known as ABX-CBL, developed by Abgenix. It binds to the antigen CD147. According to the present invention it can be administered by I.V. infusion at a dose of 20 mg/kg within 7-14 days and preferably 3-4 days prior to the administration of the stem cells.

BG9588, a humanized anti-CD40L administered at 20 mg/kg within 7-14 days and 3-4 days prior to administration of the stem cells. Administration of antibodies to CD 154, also called CD40 ligand or CD40L, is a protein that is primarily expressed on activated T cells and is a member of the TNF superfamily of molecules. It binds to CD40 on antigen-presenting cells (APC), which leads to many effects depending on the target cell type. In general, CD40L plays the role of a costimulatory molecule and induces activation in APC in association with T cell receptor stimulation by MHC molecules on the APC. In total CD40L has three binding partners: CD40, .alpha.5.beta.1 integrin and .alpha.IIb.beta.3.

(Hu5c8) 5c8, a monoclonal antibody that binds CD154 (CD40 ligand), thus blocking the interaction between CD40 and CD154, administered at 20 mg/kg within 7-14 days and preferably 3-4 days prior to administration of the stem cells.

Belimumab (registered name Benlysta previously known as LymphoStat-B), is a fully human monoclonal antibody that specifically recognizes and inhibits the biological activity of B-Lymphocyte stimulator (BLyS), also known as B cell activation factor of the TNF family (BAFF) Human Genome Sciences According to the present invention, it can be administered at a dose of 10 mg/kg within 7-14 days and preferably 3-4 days prior to administration of the stem cells.

Ipilimumab (also known as MDX-010 or MDX-101) is an anti-CTLA-4 (cytotoxic T-Cell lymphocyte-associated) human monoclonal antibody being developed by Bristol-Myers Squibb. According to the present invention, it is administered 10 mg/kg active drug within 7-14 days and preferably 3-4 days prior to administration of stem cells.

Tremelimumab (formerly ticilimumab, CP-675,206) is a fully human IgG2 monoclonal antibody produced by Pfizer. It binds to the protein CTLA-4, which is expressed on the surface of activated T lymphocytes. Tremelimumab blocks the binding of the antigen-presenting cell ligands B7.1 and B7.2 to CTLA-4, resulting in inhibition of B7-CTLA-4-mediated downregulation of T-cell activation; subsequently, B7.1 or B7.2 may interact with another T-cell surface receptor protein, CD28, resulting in a B7-CD28-mediated T-cell activation unopposed by B7-CTLA-4-mediated inhibition. Tremelimumab is administered by IV infusion at 3 mg/kg, 6 mg/kg, 10 mg/kg, 15 mg/kg within 7-14 days and preferably 3-4 days prior to administration of the stem cells.

Bertilimumab is a human monoclonal antibody that binds to eotaxin-1. (iCo Therapeutics Inc. Vancouver, B.C.) According to the present invention, it is administered at a dose of 10 mg/kg within 7-14 days and preferably 3-4 days prior to administration of stem cells.

Lerdelimumab (CAT-152) is an anti-TGF beta-2 being developed by Cambridge Antibody Technology. According to the present invention, it can be administered at a dose of 10 mg/kg within 7-14 days and preferably 3-4 days prior to administration of stem cells.

Metelimumab (CAT-192) is a human IgG4 monoclonal antibody developed by Cambridge Antibody Technology that neutralizes TGF beta 1. According to the present invention, it can be administered at a dose of 10 mg/kg preferably 3-4 days prior to administration of stem cells. Natalizumab is a humanized monoclonal antibody against the cellular adhesion molecule .alpha.4-integrin. It is co-marketed by Biogen Idec and Elan as Tysabri, and was previously named Antegren. Natalizumab is administered at a dose of 300 mg infused intravenously over approximately one hour within 7-14 days and preferably 3-4 days prior to administration of the stem cells.

Tocilizumab or atlizumab, developed by Hoffmann-La Roche and Chugai under the trade names Actemra and RoAetemra, is a humanized monoclonal antibody against the interleukin-6 receptor (IL-6R). According to the present invention, it can be administered by intravenous infusions at 8 mg/kg, within 7-14 days and preferably 3-4 days prior to administration of stem cells.

Odulimomab is a mouse monoclonal antibody directed against the alpha chain of the protein lymphocyte function-associated antigen 1 which is involved in immune reactions. It is administered 10 mg/kg active drug within 7-14 days and 3-4 days prior to administration of stem cells.

Basiliximab (trade name Simulect) is a chimeric mouse-human monoclonal antibody to the a chain (CD25) of the IL-2 receptor of T cells. Dose is 20 mg two times within 7-14 days and preferably 3-4 days prior to administration of the stem cells.

Daclizumab (trade name Zenapax) is a therapeutic humanized monoclonal antibody to the alpha subunit of the IL-2 receptor of T cells. Roche Pharmaceuticals, Hoffmann-La Roche Inc, 340 Kingsland Street, Nutley, N.J. It is administered 10 mg/kg active drug within 7-14 days and preferably 3-4 days prior to administration of stem cells.

Inolimomab is a mouse monoclonal antibody targeted against the alpha chain of the interleukin-2 receptor.OPi (formerly Orphan Pharma International). It is administered 10 mg/kg active drug within 7-14 days and preferably 3-4 days prior to administration of stem cells.

Zolimomab aritox is a mouse monoclonal antibody and is an anti-CD5 antibody which is linked to the A chain of the ricin protein (which is reflected by the aritox in the drug's name). According to the present invention, it can be administered at a dose of 10 mg/kg within 7-14 days and preferably 3-4 days prior to administration of stem cells.

Atorolimumab is mouse monoclonal antibody directed against the Rhesus factor. According to the present invention, it can be administered at a dose of 10 mg/kg within 7-14 days and preferably 3-4 days prior to administration of stem cells.

Cedelizumab is an anti-CD4 monoclonal antibody. According to the present invention, it can be administered at a dose of 10 mg/kg within 7-14 days and preferably 3-4 days prior to administration of stem cells.

Dorlixizumab is a chimeric/humanized monoclonal antibody and an immunosuppressive drag. It is administered at a dose of 10 mg/kg of active drug within 7-14 days and preferably 3-4 days prior to administration of stem cells.

Fontolizumab (trade name HuZAF) is anti-interferon gamma humanized monoclonal antibody. According to the present invention, it can be administered at an I.V. dose of fontolizumab given as 4.0 mg/kg or 10.0 mg/kg within 7-14 days and preferably 3-4 days prior to administration of the stem cells. (PDL Biopharma)

Gantenerumab is anti-beta amyloid monoclonal antibody (Roche). It is administered at a dose of 10 mg/kg of active drug within 7-14 days and preferably 3-4 days prior to administration of stem cells.

Gomiliximab is a monoclonal antibody that targets the low affinity IgE receptor (Fc.epsilon.RII or CD23). According to the present invention, it can be administered at a dose of 10 mg/kg within 7-14 days and preferably 3-4 days prior to administration of stem cells.

Maslimomab is a mouse monoclonal antibody targets the T-Cell receptor. According to the present invention, it can be administered at a dose of 10 mg/kg within 7-14 days and preferably 3-4 days prior to administration of stem cells.

Morolimumab is a human monoclonal antibody against the human Rhesus factor. According to the present invention, it can be administered at a dose of 10 mg/kg within 7-14 days and preferably 3-4 days prior to administration of stem cells.

Pexelizumab is a single chain variable fragment of a monoclonal antibody targeted against component 5 of the complement system. According to the present invention, it can be administered at a dose of 10 mg/kg within 7-14 days and preferably 3-4 days prior to administration of stem cells.

Reslizumab is an anti-IL-5 humanized monoclonal antibody. According to the present invention, It can administered as an infusion at a preferred dose of reslizumab 3.0 mg/kg within 7-14 days and preferably 3-4 days prior to administration of the stem cells. (Ception Therapeutics Inc).

Rovelizumab, also known as LeukArrest and Hu23F2G, is an anti-CD11/CD18 humanized monoclonal antibody that suppresses white blood cells. According to the present invention, it can be administered at a dose of 10 mg/kg within 7-14 days and preferably 3-4 days prior to administration of stem cells.

Siplizumab (MEDI-507) is an anti-CD2 monoclonal antibody with a human IgG1, kappa directed to CD2. The agent has shown potent immunomodulatory effects, selectively suppressing the function of T and NK cells. Siplizumab binds to CD2, a specific receptor found in T cells and NK cells, thereby triggering a host immune response that results in lysis of CD2+ cells, selective suppression of the immune system, and control of activated T cell growth. According to the present invention, Siplizumab can be administered at a preferred dose of 0.04 mg/kg i.v. and 5 or 7 mg/kg s.c. within 7-14 days and preferably 3-4 days prior to administration of stem cells. (Medimmune)

Talizumab (TNX-901) is a humanized monoclonal antibody being developed by Tanox in Houston, Tex. It was designed to target immunoglobulin E (or IgE) and IgE-expressing B lymphocytes specifically, without binding to IgE already bound by the IgE receptors on mast cells and basophils. According to the present invention, it can be administered at a dose of 10 mg/kg within 7-14 days and preferably 3-4 days prior to administration of stem cells.

Omalizumab is an anti-IgE monoclonal antibody, developed by Tanox, Novartis, and Genentech. According to the present invention, it can be administered at a dose of 10 mg/kg within 7-14 days and preferably 3-4 days prior to administration of stem cells.

Telimomab aritox is a mouse monoclonal antibody. The antibody is linked to the A chain of the ricin protein (which is reflected by the aritox in the drug's name). According to the present invention, it can be administered at a dose of 10 mg/kg within 7-14 days and preferably 3-4 days prior to administration of stem cells.

Vapaliximab is an anti-VAP-1 chimeric monoclonal antibody. According to the present invention, it can be administered at a dose of 10 mg/kg within 7-14 days and preferably 3-4 days prior to administration of stem cells.

Vepalimomab is an anti-VAPI mouse monoclonal antibody According to the present invention, it can be administered at a dose of 10 mg/kg within 7-14 days and preferably 3-4 days prior to administration of stem cells.

Abatacept (marketed as Orencia) is a fusion protein composed of an immunoglobulin fused to the extracellular domain of CTLA-4, a molecule capable of binding B7, thus preventing the full activation of T cells. Abatacept should be administered as a 30-minute intravenous infusion according to the specified dose schedule based on weight. The doses should be preferably be 500 mg for <60 kg; 750 mg for 60 kg-100 kg; and 1 gram for >100 kg within 7-14 days and preferably 3-4 days prior to the administration of the stem cells.

Belatacept (Bristol-Myers-Squibb) is a fusion protein composed of the Fc fragment of a human IgG1 immunoglobulin linked to the extracellular domain of CTLA-4, which is a molecule crucial for T-cell costimulation, selectively blocking the process of T-cell activation. It was developed by. It differs from abatacept (Orencia) by only 2 amino acids. According to the present invention, it can be administered as a 30-minute intravenous infusion according to the specified dose schedule based on weight at preferable doses of 500 mg for <60 kg; 750 mg for 60 kg-100 kg; and 1 gram for >100 kg administered within 7-14 days and preferably 3-4 days prior to administration of the stem cells.

Etanercept (trade name Enbrel, Amgen, Thousand Oaks, Calif.) is a drug that treats autoimmune diseases by interfering with the tumor necrosis factor (TNF, a part of the immune system) by acting as a TNF inhibitor. Etanercept can be administered subcutaneously (s.c.) at a dose 25 mg or 50 mg within 7-14 days and preferably 3-4 days prior to the administration of the stem cells.

Pegsunercept is a pegylated soluble tumor necrosis factor receptor. According to the present invention, it can be administered at a preferable dose of 9 mg/kg s.c, within 7-14 days and preferably 3-4 days prior to administration of the stem cells.

Aflibercept is protein comprised of segments of the extracellular domains of human vascular endothelial growth factor receptors 1 (VEGFR1) and 2 (VEGFR2) fused to the constant region (Fc) of human IgG1 with potential antiangiogenic activity and is being co-developed by Sanofi-Aventis and Regeneron Pharmaceuticals. Aflibercept (VEGF Trap), an anti-angiogenic agent, is a fusion protein specifically designed to bind all forms of Vascular Endothelial Growth Factor-A (called VEGF-A). In addition, aflibercept binds Placental Growth Factor (PLGF), which has also been implicated in tumor angiogenesis. Aflibercept can be administered by injection or IV infusion at preferable doses of 2 milligrams per kilogram (mg/kg) or 4 mg/kg, within 7-14 days and preferably administered 3-4 days prior to the administration of the stem cells.

Alefacept is a fusion protein: it combines part of an antibody with a protein that blocks the growth of some types of T cells. AMEVIVE® (alefacept) is an immunosuppressive dimeric fusion protein that consists of the extracellular CD2-binding portion of the human leukocyte function antigen-3 (LFA-3) linked to the Fc (hinge, CH2 and CH3 domains) portion of human IgG1. The preferred dosage is either 7.5 mg IV or 15 mg IM preferably administered within 7-14 days and preferably 3-4 days prior to the administration of the stem cells. Asteilas Pharma US, Inc. Deerfield, Ill. 60015.

Rilonacept also known as IL-1 Trap (marketed under the trade name Arcalyst), is a dimeric fusion protein consisting of the extracellular domain of human interleukin-1 receptor and the FC domain of human IgG1 that binds and neutralizes IL-1h. Treatment should be initiated with a loading dose of 320 mg delivered as two, 2 mL, subcutaneous injections of 160 mg each given on the same day at two different sites, within 7-14 days and preferably administered 3-4 days prior to the administration of the stem cells. Pediatric patients aged 12 to 17 years: Treatment should be initiated with a loading dose of 4.4 mg/kg, up to a maximum of 320 mg, delivered as one or two subcutaneous injections with a maximum single-injection volume of 2 mL, within 7-14 days and preferably 3-4 days prior to administration of the stem cells. Produced by Regeneron.

Dacetuzumab (also known as SGN-40 or huS2C6) is an anti-CD40 humanized monoclonal antibody. The CD40 antigen is highly expressed on most B-lineage hematologic malignancies including multiple myeloma, non-Hodgkin lymphoma and chronic lymphocytic leukemia. CD40 is also found on many types of solid tumors, including bladder, renal and ovarian cancer and on cells that play a role in immunologic disorders. It is administered at a preferred dose of 10 mg/kg of active drag within 7-14 days and preferably 3-4 days prior to administration of stem cells. Seattle Genetics, Inc.

HCD122 is a fully human antagonist anti-CD40 monoclonal antibody. CD40 is a cell-surface receptor that plays a pivotal role in immune responses, as well as cell growth and survival signaling, through its activation by CD40 ligand (CD40L). It is commonly overexpressed and activated in B-cell malignancies. According to the present invention, it can be administered at a dose of 10 mg/kg of active drug within 7-14 days and preferably 3-4 days prior to administration of stem cells. This is being developed by XOMA/NOVARTIS ONCOLOGY.

Rituximab, sold under the trade names Rituxan and MabThera, Genentech, Inc., San Francisco, Calif. is a chimeric monoclonal antibody against the protein CD20. which is primarily found on the surface of B cells. It can therefore destroy B cells. CD20 is widely expressed on B cells, from early pre-B cells to later in differentiation, but it is absent on terminally differentiated plasma cells. Rituxan is supplied at a concentration of 10 mg/mL in either 100 mg (10 mL) or 500 mg (50 mL) single-use vials. It can be administered as an infusion at a rate of 50 mg/hr. In the absence of infusion toxicity, increase infusion rate by 50 mg/hr increments every 30 minutes, to a maximum of 400 mg/hr preferably administered within 7-14 days and preferably 3-4 days prior to the administration of the stem cells. The preferred recommended dose is 375 mg/m2 as an IV infusion preferably administered 3-4 days prior to the administration of the stem cells.

Rituximab can also be administered as a Component of Zevalin® by infusing rituximab at a preferable dose 250 mg/m2 within 4 hours prior to the administration of Indium-111-(In-111-) Zevalin and within 4 hours prior to the administration of Yttrium-90-(Y-90-) Zevalin, this should be done within 7-14 days and preferably 3-4 days prior to the administration of the stem cells. Rituxan can also be administered in combination with methotrexate, preferable 3-4 days prior to the administration of the stem cells. Biogen Idec Inc. and Genentech USA, Inc.

Ibritumomab tiuxetan, sold under the trade name Zevalin, is a monoclonal antibody radioimmunotherapy targeting B-cells. The drug uses the monoclonal mouse IgG1 antibody ibritumomab in conjunction with the chelator tiuxetan, to which a radioactive isotope (either yttrium-90 or indium-111) is added. Tiuxetan is a modified version of DTPA whose carbon backbone contains an isothiocyanatobenzyl and a methyl group.

Adenosine deaminase deficiency will also lead to reduced active germinal center formation as will agents which trigger the accumulation of deoxyATP (J Immunol 171:5562-5570, 2003). Similarly, agents that enhance the expression of or activate CCR7 will lead to diminished active germinal center formation.

Stem Cells: Definitions, Isolation, Delivery and Therapeutic Uses

The term stem cell within the scope of the present invention includes any cell capable of differentiating into a desired tissue. Such cells include pluripotent stem cells, embryonic stem cells, multipotent adult stem cells, and progenitor and precursor cells. A "stem cell" is a cell from the embryo, fetus, or adult that has, under certain conditions, the ability to reproduce itself for long periods or. in the case of adult stem cells, throughout the life of the organism. It also can give rise to specialized cells that make up the tissues and organs of the body.

A "pluripotent stem cell" has the ability to give rise to types of cells that develop from the three germ layers (mesoderm, endoderm, and ectoderm) from which all the cells of the body arise. Known natural sources of human pluripotent stem cells are those isolated and cultured from early human embryos from fetal tissue that was destined to be past of the gonads.

An "embryonic stem cell" is derived from a group of cells called the inner cell mass, which is part of the early (4- to 5-day) embryo called the blastocyst. Once removed from the blastocyst the cells of the inner cell mass can be cultured into embryonic stem cells.

An "adult stem cell" is an undifferentiated (unspecialized) cell that occurs in a differentiated (specialized) tissue, renews itself, and becomes specialized to yield all of the specialized cell types of the tissue in which it is placed when transferred to the appropriate tissue. Adult stem cells are capable of making identical copies of themselves for the lifetime of the organism. This property is referred to as "self-renewal." Adult stem cells usually divide to generate progenitor or precursor cells, which then differentiate or develop into "mature" cell types that have characteristic shapes and specialized functions, e.g., muscle cell contraction or nerve cell signaling. Sources of adult stem cells include but are not limited to bone marrow, blood, the cornea and the retina of the eye, brain, skeletal muscle, dental pulp, liver, skin, the lining of the gastrointestinal tract and pancreas.

The delivery or administration of stem cells to an individual includes both the delivery or administration of exogenous stem cells as well as the mobilization of endogenous stem cells, as well as enhancing the bioavailability of spontaneously released endogenous stem cells.

Stem cells from the bone marrow are the most-studied type of adult stem cells. Currently, they are used clinically to restore various blood and immune components to the bone marrow via transplantation. There are currently identified two major types of stem cells found in bone marrow: hematopoietic stem cells (HSC, or CD34+ cells) which are typically considered to form blood and immune cells, and stromal (mesenchymal) stem cells (MSG) that are typically considered to form bone, cartilage, muscle and fat. However, both types of marrow-derived stem cells recently have demonstrated extensive plasticity and multipotency in their ability to form the same tissues. The marrow, located in the medullary cavity of bones, is the major site of hematopoiesis in adult humans. It produces about six billion cells per kilogram of body weight per day. Hematopoietically active (red) marrow regresses after birth until late adolescence after which time it is focused in the lower skull vertebrae, shoulder and pelvic girdles, ribs, and sternum. Fat cells replace hematopoietic cells in the bones of the hands, feet, legs and arms (yellow marrow). Fat comes to occupy about fifty percent of the space of red marrow in the adult and further fatty metamorphosis continues slowly with aging. In very old individuals, a gelatinous transformation of fat to a mucoid material may occur (white marrow). Yellow marrow can revert to hematopoietically active marrow if prolonged demand is present such as with hemolytic anemia. Thus hematopoiesis can be expanded by increasing the volume of red marrow and decreasing the development (transit) time from progenitor to mature cell.

The marrow stroma consists principally of a network of sinuses that originate at the endosteum from cortical capillaries and terminate in collecting vessels that enter the systemic venous circulation. The trilaminar sinus wall is composed of endothelial cells; an underdeveloped, thin basement membrane, and adventitial reticular cells that are fibroblasts capable of transforming into adipocytes. The endothelium and reticular cells are sources of hematopoietic cytokines. Hematopoiesis takes place in the intersinus spaces and is controlled by a complex array of stimulatory and inhibitory cytokines, cell-to-cell contacts and the effects of extracellular matrix components on proximate cells. In this unique environment, lympbohematopoietic stem cells differentiate into all of the blood cell types. Mature cells are produced and released to maintain steady state blood cell levels. The system may meet increased demands for additional cells as a result of blood loss, hemolysis, inflammation, immune cytopenias, and other causes.

A "progenitor or precursor" cell is partially specialized; it self-renews and also gives rise to differentiated cells. Researchers often distinguish precursor/progenitor cells from adult stem cells in that when a stem cell divides, one of the two new cells is often a stem cell capable of replicating itself again. In contrast when a progenitor/precursor cell divides, it can form more progenitor/precursor cells or it can form two specialized cells. Progenitor/precursor cells can replace cells that are damaged or dead, thus maintaining the integrity and functions of a tissue such as liver or brain.

Means for isolating and culturing stem cells useful in the present invention are well known. Umbilical cord blood is an abundant source of hematopoietic stem cells. The stem cells obtained from umbilical cord blood and those obtained from bone marrow or peripheral blood appear to be very similar for transplantation use. Placenta is an excellent readily available source for mesenchymal stem cells. Moreover, mesenchymal stem cells have been shown to be derivable from adipose tissue and bone marrow stromal cells and speculated to be present in other tissues. Amniotic fluid and tissue is another excellent source of stem cells. While there are dramatic qualitative and quantitative differences in the organs from which adult stem cells can be derived, the initial differences between the cells may be relatively superficial and balanced by the similar range of plasticity they exhibit. For instance, adult stem cells both hematopoietic and mesenchymal, under the appropriate conditions can become cardiac muscle cells. Delineation of full range of potential for adult stem cells has just begun. Stem cells may be isolated and differentiated using known methods. For example, in mice, bone marrow cells are isolated by sacrificing the mouse, cutting the leg bones with a pair of scissors, and flushing the stem cells out. Stem cells may also be isolated from bone marrow cells by panning the bone marrow cells with antibodies which bind unwanted cells, such as CD4+ and CD8+(T cells), CD45+(panB cells), GR-1 (granulocytes). For an example of this protocol see, Inaba et al., J. Exp. Med. 176:1693-1702 (1992).

BRIEF DESCRIPTION OF THE DRAWINGS

FIG. 1 shows a typical view of layers resulting from gradient centrifugation of whole blood. 1 shows the platelets; 2 the buffy coat with MNCs and stem cells; 3 the ficoll; and 4 the RBC pellet and stem cells.

SUMMARY OF THE INVENTION

In humans, CD34+ hematopoietic stem cells can be obtained from a variety of sources including cord blood, bone marrow, and mobilized peripheral blood. Purification of CD34+ cells can be accomplished by antibody affinity procedures. An affinity column isolation procedure for isolating CD34+ cells is described by Ho et al., Stem Cells 13 (suppl. 3): 100-105(1995). See also, Brenner, Journal of Hematotherapy 2: 7-17 (1993). Methods for isolating, purifying and culturally expanding mesenchymal stem cells are known. Specific antigens for MSC are also known (see, U.S. Pat. Nos. 5,486,359 and 5,837,539).

Stem cells are characterized by the ability to renew themselves through mitotic cell division and to differentiate into a diverse range of specialized cell types. Stem cells exist along a range of potencies. Totipotent stem cells are cells such as a fertilized egg that can generate ail tissues necessary for development of a complete organism. Pluripotent stem cells are cells that can give rise to stem cells for all 3 germ layers and include cells such as embryonic stem cells, spermatogonial stem cells (Cell. 119(7):1001-1012, 2009; NATURE 440:1199-1203, 2006), or induced pluripotent stem cells that when injected into tetraploid embryo can give rise to an entire organism (Stem Cell Rev. 2010), but not to the extra-embryonic tissues needed, such as the placenta. Very-small embryonic like stem cells are cells found within the bone marrow, blood, heart and other tissues of the adult that can give rise to cells of cells from all 3 germ layer lineages, however, they have not yet been shown in tetraploid complementation assays to generate an entire organism, so it is unclear if they are true pluripotent stem cells for which somatic imprinting prevents their activity in tetraploid complementation or whether they are more restricted yet extremely plastic multipotent stem cells (DEVELOPMENTAL DYNAMICS 236:3309-3320, 2007). Multipotent stem cells are cells such as hematopoietic stem cells (HSC) (J Exp Med. 207(6): 1127-1130, 2010), adipose stem cells (ASC) (Stem Cells Dev. 2010 [Epub ahead of print]) (6) or mesenchymal stem cells (MSC) (StemBook, Cambridge (Mass.): Harvard Stem Cell Institute; 2008-2009) that can give rise to a variety of functioning cells within restricted lineages.

Stem cells can be further characterized by the degree to which they can differentiate and are distinguished by their potency. Potency specifies the differentiation potential (the potential to differentiate into different cell types) of the stem cell.

Totipotent (a.k.a omnipotent) stem cells can differentiate into embryonic and extraembryonic cell types. Such cells can construct a complete, viable, organism. These cells are produced from the fusion of an egg and sperm cell. Cells produced by the first few divisions of the fertilized egg are also totipotent.

Pluripotent stem cells are the descendants of totipotent cells and can differentiate into nearly all cells, i.e. cells derived from any of the three germ layers.

Multipotent stem cells can differentiate into a number of cells, but only those of a closely related family of cells.

Oligopotent stem cells can differentiate into only a few cells, such as lymphoid or myeloid stem cells.

Unipotent cells can produce only one cell type, their own, but have the properly of self-renewal that distinguishes them from non-stem cells (e.g. muscle stem cells).

The two broad types of mammalian stem cells are: embryonic stem cells that are isolated from the inner cell mass of blastocysts, and adult stem cells that are found in adult tissues.

Adult stem cells are undifferentiated cells, found throughout the body after embryonic development, that multiply by cell division to replenish dying cells and regenerate damaged tissues. Also known as somatic stem cells, they can be found in juvenile as well as adult animals and humans. The types of adult stem cells include hematopoietic stem cells, mammary stem cells, mesenchymal cells, endothelial stem cells, neural stem cells, olfactory adult stem cells, adipose-derived stem cells, neural crest stem cells, and testicular stem cells.

Progenitor cells have a tendency to differentiate into a specific type of cell. In contrast to stem cells, however, they are already far more specific: they are pushed to differentiate into their "target" cell. The most important difference between stem cells and progenitor cells is that stem cells can replicate indefinitely, whereas progenitor cells can only divide a limited number of times. Controversy about the exact definition remains and the concept is still evolving.

The terms "progenitor cell" and "stem cell" are sometimes equated.

Stem cells found within the mononuclear fraction of whole blood, bone marrow, adipose tissue, umbilical cord blood, and either tissues, as well as isolated stem cells from these mononuclear fractions have been demonstrated to provide a benefit to human patients. A peripheral blood mononuclear cell (PBMC) is any blood cell having a round nucleus. For example: a lymphocyte, monocyte or a macrophage. These blood cells are a critical component in the immune system to fight infection and adapt to intruders. The lymphocyte population consists of T cells (CD4 and CDS positive .about.75%), B cells and NK cells (.about.25% combined). PBMCs are often extracted from whole blood using ficoll, a hydrophilic polysaccharide that separates layers of blood, with monocytes and lymphocytes forming a buffy coat under a layer of plasma. This huffy coat contains the PBMCs. Additionally, PBMC can be extracted from whole blood using a hypotonic lysis which will preferentially lyse red blood cells. This method results in neutrophils and other polymorphonuclear (PMN) cells, which are important in innate immune defence being obtained. PBMC fractions of bone marrow aspirates have been used to treat patients following a myocardial infarction, and have been shown to reduce subsequent mortality and to slightly improve cardiac function in these patients (Eur Heart J 27:2775-2783, 2006). While mortality is significantly reduced by these types of treatments, cardiac function is only slightly improved. Nuclear imaging studies on these patients have shown that the majority, up to 97%, of the intra-coronary injected mononuclear fraction stem cells do not remain in the heart, but can be found predominantly in the spleen and liver within 60 to 90 minutes after injection (Circulation 111:2198-2202, 2005). Other imaging studies have likewise demonstrated that stem cells found within the mononuclear fraction of whole blood, bone marrow, adipose tissue, umbilical cord blood, placenta, amniotic fluid, and other tissues, as well as isolated stem cells from these mononuclear fractions, accumulate in the spleen in many different species (STEM CELLS 24:2279-2283, 2006; J Nucl Med 45:512-518, 2004; J Nucl Med 47:1212-1239, 2006; J Nucl Med 47:1295-1301, 2006).

Animal studies have demonstrated that administration of higher numbers of bone marrow mononuclear cells leads to improved cardiac repair and functional recovery (Circulation 114:2163-2169, 2006). However, for the clinical patient, this would require aspiration of large volumes of bone marrow, up to 200 mls, under general anesthesia, and this is considered highly undesirable for recent post-infarct patients whose heart function remains depressed. Investigators have also tried to concentrate the stem cells they are injecting in order to obtain better organ targeting and retention. While enriching the number of CD34+ cells injected has led to higher accumulation of CD34+ cells in the heart after intra-coronary injection, this method to enhance stem cell delivery is thought to be sub-optimal because it is not known at this time which particular stem cells contained within the mononuclear cell fraction are necessary for tissue regeneration (Circulation 111:2198-2202, 2005). Furthermore, purified human mesenchymal stem cells (MSC) have been shown to augment the engraftment of human umbilical cord blood CD34+ stem cells (Hematology VOL 14 NO 3:125-132, 2009).

Stem cells may be autologous or from an unrelated donor. Stem cells may be contained within the mononuclear cell fraction from bone marrow, whole blood, umbilical cord blood, adipose tissue or other sources, or they may be purified by selection for CD34, CD133, CD105, CD117, SSEA1-4, dye exclusion or other specific stem cell antigens. Stem cells can be isolated from whole blood, bone marrow, umbilical cord blood, adipose tissue, tissue scrapings from the olfactory mucosa and other stem cell sources that can be dissociated into single cell suspensions, such as umbilical cord tissue, by density gradient centrifugation using Ficoll-Hypaque or other commercially available gradients. Stem cells can be recovered from the mononuclear cell fraction resulting from such procedures. Alternatively, stem cells can be found within other fractions after density gradient centrifugation (Stem Cells and Development 2011 Bhartiya et. al.) For instance, umbilical cord blood can be diluted 1:1 in PBS, carefully overlaid onto Histopaque 1077 (Sigma) and centrifuged at 1500 rpms at room temperature for 30 minutes. The resulting layers as depicted in FIG. 1 cat) be further processed for stem cell isolation. Layer 1 is the platelet layer, layer 2 is the buffy coat containing mononuclear cells, layer 3 is the Ficoll layer, and layer 4 is the red blood cell pellet layer. Layers 1, 2, and 3 can be collected, diluted with appropriate media such as DMEM F12 with or without FBS and centrifuged again to obtain the cell pellet. Layer 4 can be diluted with appropriate media such as DMEM F12 and centrifuged at 800 rpm for 15 minutes at room temperature in a standard benchtop centrifuge. Stem cells can be recovered predominantly from layer 2 (Buffy coat) and layer 4 (RBC pellet).

Stem cells can be further characterized and isolated by specific antigens expressed on their surface using cell sorters such as the ARIA from BD, using magnetic columns such as those available from Miltenyi, using magnetic beads and DYNAL magnets and other antibody/antigen based separation methods known to those skilled in the art. Stem cells can also be identified and isolated by their ability to bind to other cells as described in this disclosure.

Pluripotent stem cells can be characterized by the expression of stage-specific embryonic antigen (SSEA), the transcription factors Oct4 and Nanog and other markers. Hematopoietic stem cells are characterized by expression of markers such as CD34, CD133, ckit, Sca1, and are also CD45 positive. The abbreviation CD refers to an antigen family and means "cluster of differentiation".

Hematopoietic stem cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). The hematopoietic tissue contains cells with long-term and short-term regeneration capacities and committed multipotent, oligopotent, and unipotent progenitors. HSCs constitute 1:10.000 of cells in myeloid tissue. HSCs express the following antigens: CD34, CD90 (Thy1), CD45, CD41, CD305, CD117 (c-kit), SCF (kit ligand), Ly6A/E (sca-1), CD127, CD44, CD33, CD38, CD14, CD106, CD84, CD90, Flk-1, CD164, Notch1, CD338 (ABCG2), CD202b, CD184, AC133 (=CD133), and CXCR4.

Mesenchymal stem cells, or MSCs, are multipotent stem cells that can differentiate into a variety of cell types, including: osteoblasts (bone cells), chondrocytes (cartilage cells) and adipocytes (fat cells). Mesenchymal stem cells are characterized by the expression of CD45, CD90, CD105, CD34, CD31, CD29, CD106, CD44, CD51, CD166, Ly6A/E (sca-1), CD117, CD71, CD10, CD49d, CD49e, TNAP, PTP LAR, W5C5 antigen, W3D5 antigen, W4A5 antigen, and CXCR4.

Endothelial stem cells (or endothelial progenitor or precursor cells) are multipotent stem cells. They are one of the three types of stem cells to be found in bone marrow and express the following antigens: CD45, CD31, CD34, CD105, CD146, CD106, CD54, CD117, CD102, CD120a, CD120b, CD14, CD29, CD49d, CD49e, CD49f, CD62P, CD62L, and CXCR4.

Neural stem cell (NSCs) are the self-renewing, multipotent cells that generate the main phenotypes of the nervous system. Neural progenitor and stem cells have been isolated from the striatal tissue, including the subventricular zone—one of the neurogenic areas—of adult mice brain tissue and from various areas of the adult brain, including non-neurogenic areas, such as the spinal cord, and from various species including human. NSCs express the following antigens: CD29, CD146, Notch1, Ki67, CD24, CD49f, Vimentin, CD81 and CXCR4. Neural Progenitor Cells express the following antigens: 57D2 antigen, W4A5 antigen and CXCR4.

Embryonic, Spermatogonial, Testicular and Pluripotent Stem Cells such as from iPS, SCNT, ANT-OAR express the following antigens: CD24, CD9, Nanog, Smad, Runx2, c myc, CD30, GSC, Oct3/4, Sox2, SSEA 1 (CD15), SSEA 4, CD324, CD29, Tra-1-60, Tra-1-81, CD338 (ABCG2), CD49f, FoxD3, Stat3, Hox11, and CXCR4.

VSELs are positive for SSEA1, Oct4, Nanog, Rex1 and other pluripotent stem cell markers, and for CD133, CD34, AP, cMet, LIF-R, and CXCR4. (J Am Coll Cardiol 53(1): 10-20, 2009; Stem Cell Rev 4:89-99, 2008). Additionally, novel stem cells are routinely being identified that are characterized by distinct markers such as the Hox11+ stem cells found in the adult spleen (Horm Metab Res 40: 137-146, 2008). A fetal stem cell remaining in the adult spleen has been identified that is capable of regenerating pancreatic islet cells, however, this cell is present in the CD45 negative fraction of the spleen (Mol Cell Proteomics 4(10): 1459-1470, 2005). The Hox11+ splenic cells, while negative for CD45, do express OCT3/4, SOX2, KLF4, c-MYC and NANOG, making them potentially equivalent to embryonic stem cells and induced pluripotent stern cells (iPS) (Int J Biochem Cell Biol. 2009 Dec. 18.

Therapeutic Uses of Stem Cells

Stem cell therapy is being investigated and perfected for the treatment of many diseases. Conditions which could benefit from stem cell therapy include: ocular disease, neural disease. GI diseases, musculoskeletal disease, metabolic diseases, endocrine diseases, vascular diseases, pulmonary diseases, cardiac diseases, cardiovascular diseases, immune mediated diseases, auto-immune mediated diseases, cardiovascular diseases, and all diseases for which regenerative therapy would be of benefit. Clinical trial information contained on the NIH website www.clinicaltrials.gov lists over 3000 stem cell investigations. Diseases under evaluation include: vasculitis, rheumatic disorders using endothelial progenitor cells, therapeutic neovascularization by the implantation of autologous mononuclear cells in patients with connective tissue diseases, repeated administrations of granulocyte colony stimulating factor for blood stem cells mobilization in patients with progressive supranuclear palsy, corticobasal degeneration and multiple system atrophy; hematological malignancies, leukemias, lymphomas, cancers, osteopetrosis, aplastic anemia and cytopenias, sickle cell disease and thalassemia, limbal stem cell deficiency, breast cancer, acute myocardial infarction (See U.S. Pat. No. 7,862,810 isolating and culturing cardiac stem cells that are c-kit positive) coronary artery disease (See U.S. Pat. No. 7,470,538 isolating and administering by infusion into the coronary artery enriched CD133.sup.+/CD34.sup.+/CXCR4.sup.− cells isolated from umbilical cord blood), peripheral vascular disease, heart failure, type I diabetes mellitus (See U.S. Patent Application Publication No. 2011000830, Human Adipose Derived Insulin Making Mesenchymal Stem Cells For Treating Diabetes Mellitus), type 2 diabetes mellitus, stroke, spinal cord injury, neuroblastoma, multiple sclerosis (See U.S. Patent Application Publication No. 20100166712, administering autologous mesenchymal stem cell-derived neural precursors to treat MS), systemic sclerosis, lupus erythematosus, chronic wound healing, burns, fracture healing, cartilage repair, CNS tumors, osteoarthritis, renal failure, Parkinson's Disease (See U.S. Patent Application Publication No, 20100010087. Methods for Inducing Stem Cell Migration and Specialization with EC-18), myelomas, diabetic foot, liver and biliary cirrhosis, dilated cardiomyopathy, anemia, retinitis pigmentosa, Crohn's Disease, diabetic neuropathy, mastocytosis, ovarian cancer, epilepsy, myasthenia gravis, autoimmune diseases, granulomatous disease, osteonecrosis, liver failure, PMD disease, lypodystrophy, demyelinating diseases, cartilage defects, retinal disease, lupus nephritis, Alzheimer's Disease, traumatic brain injury, sarcoma, myositis, hyperglycemia, macular degeneration, ulcerative colitis, muscle degeneration, and others. Limitations to these stem cell therapies include an inability to optimally deliver and engraft stem cells, whether to a specific injured organ or to hematopoietic centers in the bone marrow and spleen.

Delivery of Exogenous Stem Cells

Stem cells may be delivered to a patient by many routes. For instance, stem cells, in an appropriate excipient that optimizes stem cell viability and eliminates cell clumping, may be administered by intravenous, intra-arterial, intramuscular, intradermal, subcutaneous, intraperitoneal, intrapericardial, intraocular, transvascularly, transendocardially, transepicardially, transeptally, epicardially, by transcoronary vein, by percutaneous transmyocardial revascularization, intrathecal, intra-organ, intranasal, intraventricle, or intra-epidural via needle, catheter or other minimally invasive method. Stem cells may also be administered by these routes in a 'matrix' mixture or suspension mixture designed to help retain stem cells at the site of injection, for instance a collagen, fibrinogen, fibronectin, laminin, alginate, agarose, methylcellulose, liposomal, nanoparticle, micelle, albumin bubble, fatty acid, or other semi-solid suspension formulation.

Catheter based delivery systems that can be used to deliver stem cells include standard balloon angioplasty infusion catheters, percutaneous coronary artery delivery catheters, stop flow inflations of over-the-wire balloon catheters, Swan Ganz type catheters, Hickman type catheters, Foley type catheters, central venous catheters, pigtail type catheters, SmartPort™ systems, metal-tipped magnet guided catheters such as the Gentle Touch Magnetic Navigation System developed by Stereotaxis Inc or the Mitralign, the Accucinch System, and by catheters that inject directly into an organ such as the HELIX™, the MyoCath™, NOGA R-guided Myostar™, the Stiletto™, or the intravascular ultrasound (IVUS) guided TransAccess Delivery System™, or catheters that deliver via arterial routes such as the OpenSail™, Concerto™, Microsyringe infusion catheter from Mercator, and Maverick™, or via implantable device therapies such left ventricular assist devices (LVADs), biventricular assist devices (BiVADs), the Optimizer™, cell-delivery catheters such as described in US 2009/0299269.

Stem cells may also be administered to a patient using invasive surgical means, and then injected directly into the organ or applied to the organ. Applications to apply the stem cell composition to an organ include collagen matrices, extracellular matrix compositions, biopolymer microthreads made of fibrin or other extracellular matrix material, patches containing extracellular matrix and biodegradable materials, fibrin patches, alginateor agarose based patches, scaffolds composed of extracellular matrix materials and biodegradable physiologically inert material that could include components such as dextrans, coating stem cells with organ specific antigens or binding molecules, remnant extracellular matrices also known as scaffolds or decellularized organs from ex vivo digested organ donors or cadaveric organs, and contact lenses among others.

Mobilization of Endogenous Stent Cells

Another method to treat patients with stem cells involves mobilizing their own body's stem cells to exit organs, such as the bone marrow, and enter the circulation. For example, therapeutics such as granulocyte colony stimulating factor (G-CSF; Filgrastim) which is sold as Neupogen or in longer acting forms such as Neulasta, granulocyte-macrophage colony stimulating factor (GM-CF8; Sargramostim) which is sold as Leukine, AMD3100 which is sold as Mozobil/Plerixafor by Genzyme Corporation, cause stem cell numbers within the circulation to increase. Neupogen comes in single use vials or single use syringes containing either 300 or 480 micrograms Filgrastim. The excipient is composed of acetate, sorbitol, polysorbate 80, sodium and water for injection. Neupogen is used clinically as an intravenous twice daily dose, a subcutaneous once daily-dose or a chronic subcutaneous treatment. Neupogen is approved to accelerate recovery of neutrophil counts in cancer patients receiving myelosuppressive chemotherapy, in patients with Acute Myeloid Leukemia receiving induction or consolidation chemotherapy, in cancer patients receiving bone marrow transplant, in patients with severe chronic neutropenia, and in patients undergoing peripheral blood progenitor cell collection and therapy. Neupogen is typically administered on a daily basis between 3 and 69 micrograms per kilogram body weight starting 4 days after chemotherapy with treatment lasting for 2 to 20 days. According to the package insert for Neupogen, G-CSF regulates the production of neutrophils within the bone marrow and affects neutrophil progenitor proliferation, differentiation, and selected end-cell functional activation (including enhanced phagocytic ability, priming of the cellular metabolism associated with respiratory burst, antibody dependent killing, 7 and the increased expression of some functions associated with cell surface antigens). G-CSF has also been shown to mobilize stem cells into the circulation by: its action to reduce CXCL12 expression on the bone marrow stroma and to reduce CXCR4 expression, by leading to a clipping of the N terminus of CXCR4 (1), by reducing VCAM expression in the bone marrow (2) G-CSF has been shown to increase CXCL2, the cognate ligand for CXCR2, Since it's approval for clinical therapy, G-CSF has also been shown to increase the number of very small embryonic-like stem cells in the circulation.

According to the package insert, LEUKINE is indicated for the mobilization of hematopoietic progenitor cells into peripheral blood for collection by leukapheresis. Mobilization allows for the collection of increased numbers of progenitor cells capable of engraftment as compared with collection without mobilization. After myeloablative chemotherapy, the transplantation of an increased number of progenitor cells can lead to more rapid engraftment. which may result in a decreased need for supportive care. Myeloid reconstitution is further accelerated by administration of LEUKINE following peripheral blood progenitor cell transplantation. The recommended dose of LEUKINE is 250 micrograms permeter square body surface area per day, administered as a 24 hour intravenous infusion or once daily subcutaneously. The optimal treatment time with LEUKINE is apparently 5 days for stem cell mobilization into the circulation. Leukine has also been shown to be effective in combination with G-CSF in patients who were poor mobilizers in response to G-CSF alone.

Mobozil has the chemical name 1,1'-[1,4-phenylenebis(methylene)]-bis-1,4,8,11-tetraazacyclotetradecane. It has the molecular formula C28H54N8. Mobozil is an inhibitor of the chemokine receptor CXCR4, and blocks binding of its cognate ligand SDF-1 (CXCL12). Mobozil causes circulating stem cell numbers to increase by disrupting the binding of stem cell expressed CXCR4 to SDF-1 (CXCL12) expressed by the stromal and other cells of the bone marrow. Optimal mobilization after Mobozil treatment relies on complement activation. Subcutaneous injection of Mobozil is approved for use in combination with Neupogen to mobilize hematopoietic stem cells to the peripheral blood for collection and subsequent autologous transplantation in patients with non-Hodgkin lymphoma (NHL) and multiple myeloma (MM), Mozobil is sold as a single-use vial containing 1.2 mL of a 20 mg/mL solution. Patients are treated with Mozobil according to the following recommended schedule as detailed in the package insert: initiate Mozobil treatment after the patient has received G-CSF once daily for 4 days; repeat Mozobil dose up to 4 consecutive days; select dose based on 0.24 mg/kg actual body weight; administer by subcutaneous injection approximately 11 hours prior to initiation of apheresis. The combination of G-CSF and Mobozil has been shown to mobilize more primitive stem cells into the circulation than the use of G-CSF alone.

Other agents known to mobilize stem cells, including hematopoietic stem cells, into the cirulcation include hepatocytre growth factor (HGF) erythropoietin, parathyroid hormone, Flt3-ligand, stem cell factor (SCF). Other agents known to or that would be expected to result in increased mobilization of stem and progenitor cells into the circulation include; agents that increase stem cell proliferation such as colony stimulating factors, agents that increase endogenous G-CSF production such as Maitake beta-glucan, agents that reduce the expression of SDF-1 or CXCR4 including CXCR4 down-regulating agonists, agents that reduce the binding affinity of SDF-1 or CXCR4, agents that attenuate the signaling of CXCR4, agents that block bioaccumulation of stem cells away from the circulation, agents that enhance the egress of stem cells into the circulation such as activation of complement or increasing plasma sphingosine-1-phosphate, agents that upregulate the expression of CXCR2 in the bone marrow or its cognate ligand CXCL2, agents that reduce VCAM expression in the bone marrow such as the chemotherapeutic cyclophosphamide, retinoic receptor agonists, small molecule inhibitors of VLA-4 such as BIOS 192 or other blockers of VLA4, metalloproteinase or carboxypeptidase activators that would degrade bone marrow expressed CXCL12, or selected chemotherapy regimens, or regimens adding cyclophosphamide or the topoisomerase inhibitor etoposide to G-CSF treatment, ingestion of fucoidan, by the chemokine CXCL2, and colominic acid, among others.

Spontaneously Released Endogenous Stem Cells

Another method to treat patients with stem cells involves preventing spontaneously released endogenous stem cells from sequestering in the lymphatic tissues. Stem and progenitor cells are spontaneously released into the blood stream on a daily basis. Experiments using parabiotic mice have demonstrated that the spleen readily exchanges stem and progenitor cells with the circulation. Additionally, disease states have been demonstrated to lead to increased levels of circulating stem and progenitor cells, for instance, hypercholesterolemia, heart attack, STEMI or CAD, arterial ligation or transient ischemia, sojourn at moderate altitude, primary hyperparathyroidism, and retinal pigment epithelium damage, among others. Preventing spontaneously released or disease-induced stem cells from sequestering in lymphatic tissues will make more stem cells available for regeneration of damaged tissues or organs.

Compositions and Methods for Regenerating Germinal Centers in Lymphatic Tissues

The present invention fills this need by providing for methods and compositions for regenerating, rejuvenating and increasing the number of germinal centers in lymphatic tissues after radiation or chemotherapy. Therapeutics that Rejuvenate or Regenerate the Germinal Centers in Lymphatic Tissues according to the present invention include immune activators, co-stimulatory molecules, immune adjuvants and combinations thereof.

In one embodiment of the present invention germinal centers in lymphatic tissues are regenerated by the administration of adjuvants. Examples of such adjuvants include pathogen-associated molecular patterns, liposome, lipopolysaccharides, molecular cages for antigen, components of bacterial cell wails, endocytosed nucleic acids such as double-stranded RNA (dsRNA). single-stranded DNA (ss-DNA), and unmethylated CpG dinucleotide-containing DNA, mineral salts such aluminum hydroxide (alum), aluminum phosphate, calcium phosphate, aluminum hydroxide, aluminum potassium phosphate, aluminum sodium hydrogen phosphate, and aluminum hydroxyphosphate sulfate. Other adjuvants include oil-in-water emulsions such as squalene, montanide ISA720 (squalene) or ISA 51 (Drakeol), MF59 (Novartis) and SBAS2. Another class of adjuvants which can be used according to the present invention is particulate adjuvants such as virosomes, saponins and lipids including microbial derivatives such as monophosphoryl lipid A CpG motifs, BCG-primed immunity called BCG-CWS (*Mycobacterium bovis*).

Lipopolysaccharides and mitogens such as Concanavalin A., components of bacterial cell walls, archaeosomes (ether glycerolipids of the archaeon *Methanobrevibacter smithii*), the TLR4 agonist GLA glucopyranosyl lipid adjuvant, LPS and BCG (Immune Design) the TLR2 agonists BCG, peptidoglycan, and gram positive bacteria, the TLR5 agonist flagellin, schistosome egg antigens (SEAs), *listeria monocytogenes* (LM). Other adjuvants include Toll-like receptor agonists and activators including CpG oligonucleotides of lengths up to 100 bases, most preferably of lengths of 20 bases, TLR1 agonists such as Pam3Cys, TLR2 agonists such as Pam3Cys; TLR3 agonists such as dsRNA and poly PC, TLR7 agonists such as imidazolequinolenes for example Imiquimod (R-839) and Resiquimod (R-848), TLR8 agonists such as Resiquimod (R-848); and TLR9 agonists such as poly I:C and CpG. Also included within the present invention are the use of plant derivative adjuvants, beta-glucan, saponin based QS21, and concanavalin A.

Another embodiment of the present invention is comprised of methods to augment the numbers of active germinal centers in the spleen to enhance stem cell transplant engraftment and hematological recovery in patients undergoing cancer therapy, non-myeloablative therapy or myeloablative therapy, including chemotherapy, radiation, and combination treatments. Increased numbers of active germinal centers leads to enhanced stem cell binding and engraftment in the spleen and subsequently accelerated rates of hematopoietic recovery following chemotherapy conditioning regimens and cancer treatments. In addition to treatment of cancer and leukemias, non-myeloablative therapy is used for treatment of autoimmune diseases (Pediatr Clin North Am. 57(1):239-71, 2010) including type I diabetes (JAMA. 297(14):1568-1576, 2007), lupus and multiple sclerosis (www.clinicaltrials.gov). The present invention provides methods to enhance hematopoietic recovery in cancer or autoimmune patients undergoing myeloablative or non-myeloablative conditioning by increasing the numbers of splenic germinal centers and thereby augmenting transplanted stem cell binding, engraftment and proliferation. For example, patients undergoing stem cell treatment following myeloablative or non-myeloablative conditioning regimens are at risk of infection and death during the time required for administered stem cell engraftment and hematopoietic regeneration. Acceleration and augmentation of stem cell engraftment by increasing the numbers of germinal centers available for stem cell binding in the spleen can reduce the time required for hematopoietic recovery and thereby diminish risk of infection and death in these patients.

Stem cells may be autologous or from an unrelated donor. Stem cells may be contained within the mononuclear cell fraction from bone marrow, whole blood, umbilical cord blood, adipose tissue or other sources, or they may be purified by selection for CD34, CD133, CD 105, CD117, SSEA1-4, dye exclusion or other specific stem cell antigens.

Splenic germinal centers can be specifically increased by treatments which activate the CD40 receptor (Blood. 104: 4088-4096, 2004; J. Clin. Invest. 112:1506-1520 2003) (50) (51). The functional receptor is a CD40 trimer or multimer with TNFR1 or TNFR2 components. Examples of treatments that activate the CD40 receptor include: Agonistic antibodies to CD40 activate the CD40 receptor, appropriate conformations of solCD40L may activate the CD40 receptor, and agents which increase the expression of CD40 receptor by altering transcription rates such as via AT-hook transcription factor AKNA, mRNA stability or protein stability can also lead to increased activity and signaling. Alternatively, members of the TRAF and TTRAP families interact with CD40 receptor and mediate its signaling, leading to enhanced active germinal center slumbers. Agents which activate germinal center B cell cyclo-oxygenase 2 or the EP2 receptor replicate CD40 receptor engagement and can lead to enhanced active germinal center formation. Other means to activate germinal center formation and persistence include inhibition or loss of CCR7 (J. Leukoc. Biol. 85: 409-417, 2009). Other means to activate germinal center formation and persistence include inhibition or loss of CCR7 (J. Leukoc. Biol. 85: 409-417, 2009).

In another embodiment of the present invention is comprised of administering immunostimulatory molecules to promote regeneration of the germinal centers in lymphatic tissue. Immunostimulatory molecules may be antibodies, fusion proteins, soluble ligands, small molecules, transcription regulators, mRNA or protein stabilizers, and other immunostimulatory moieties. For instance, the co-stimulatory CD28 pathway can be activated by soluble B7 proteins and an antibody such as with TeGenero 1412 compound.

TGN1412 is a humanized monoclonal antibody designed as an agonist of the CD28 receptor on T lymphocytes, which stimulates the production and activation of T lymphocytes. Boerhinger Ingelheim manufactured the TGN1412.

Additional co-stimulatory molecules and pathways include OX40/OX40 ligand, 4-1BB/4-1BB ligand, the B7/CD28 family; B7-1/CD80, CD28, B7-2/CD86, CTLA-4, B7-H1/PD-L1, ICOS, B7-H2, PD-1, B7-H3, PD-L2/B7-DC, B7-H4, PDCD6, BTLA, the Co-stimulatory TNF Superfamily Molecules; 4-1BB/TNFRSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40 Ligand/TNFSF5, GITR/TNFRSF18, GITR Ligand/TNFSF18, HVEM/TNFRSF14, LIGHT/TNFSF14, OX40/TNFRSF4, OX40 Ligand/TNFSF4, and TACI/TNFRSF13B, the SLAM Family; 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD 150, and other Co-stimulatory Molecules; CD2, CD53, CD82/Kai-1, CD90/Thy1, CD96, CD160, Ikaros, Integrin alpha 4/CD49d, Integrin alpha 4 beta 1, Integrin alpha 4 beta 7/LPAM-1, LAG-3, LMIR1/CD300A, CRTAM, DAP12, Dectin-1/CLEC7A, DPPIV/CD26, EphB6, TCL1A, TIM-1/KIM-1/HAVCR, TIM-4, TSLP, TSLP R, HLA-DR, and ephrins.

Other agents that may enhance germinal center regeneration are agents known to cause cytokine burst such as the Anti-CD20 (Rituximab).

Other immune-activating agents may include agonists to the IL21 receptor, with agonistic antibodies.

Other adjuvants used preclinically or clinically include:

Endocytosed nucleic acids such as double-stranded RNA (dsRNA), single-stranded DNA (ssDNA), and unmethylated CpG dinucleotide-containing DNA.

Adenovirus and adenovirus components such as adenovirus type 5 (Ad5).

Agonists and activators of retinoic acid-inducible gene (RIG)-1-like receptors (RLR).

P2X1, P2X4, or P2X7 activators or agonists.

Agonists and activators of nucleotide-binding oligomerization domain-like receptors (NLR).

Advax, liposomes, chitosan microspheres and dimethyldioctyldecyl ammonium bromide (DDA).

Most newer human adjuvants in development are ISCOMS, QS21, AS02, and AS04.

$ASO_4$ is deacylated monophosphoryl lipid A MPL plus aluminum.

CpG oligonucleotides can be of lengths up to 300 bases, most preferably of lengths of 20 bases.

Anti-CD3 OKT3 can also be administered intravenously (i.v.) to induce regeneration of germinal cells within lymphatic tissues.

The present invention is also comprised of administering two or more therapeutic agents to generate germinal centers within lymphatic tissues. In another embodiment of the present invention, stem cells are administered in conjunction with the therapeutic agent that regenerates the germinal centers.

Dosing of Adjuvants

Aluminum potassium phosphate can be administered at a dose of about 0.17 mgs.

Aluminum phosphate can be administered at a dose of about 1.5 mgs.

Aluminum hydroxide can be administered at a dose of about 0.15 mgs to about 0.3 mgs. Aluminum salts in general can be administered at doses as high as 0.85 mgs.

Aluminum hydroxyphosphate can be administered at a dose of about 0.225 mgs.

As a combination Aluminum hydroxide and Aluminum phosphate can be administered at a combined dose of about 0.45 mgs.

Dosing of Oil Emulsions

SBAS-2 is an oil-in-water emulsion of MPL and QS21.

Oil-in-water emulsions such as montanide ISA720 (squalene) or ISA 51 (Drakeol).

Squalene is in MF59 adjuvant used by Novartis and dosed at 1.95% or 2 parts per hundred or at 4 grams per 100 mls for an 0.5 to 1 ml injection for adjuvant activity, MF59 adjuvant contains (Lipovant; 4-5% w/v squalene, 0.5% w/v Tween 80, 0.5% Span 85, and optionally, varying amounts of muramyl tripeptide phosphatidyl-ethanolamine (MTP-PE), which activates non-TLR sensing receptors known as NOD-LRRs).

Dosing of Microbial Derivatives

BCG-primed immunity called BCG-CWS (*Mycobacterium bovis*) 1 to $8.\text{times}.10.\text{sup}.8$ colony forming units (CFU) per vial for adults, half the dosage for children.

Archaeosomes (ether glycerolipids of the archaeon Methanobrevibacter *smithii*) dosed at 0.1 to 500 micrograms per gram body weight and most preferably at 38 micrograms per mg body weight.

Dosing of Toll-Like Receptor Agonists and Activators

CpG oligonucleotides of lengths up to 100 bases, most preferably of lengths of 20 bases, dosed at 1, 10, 100, 500 micrograms per 20-25 grams body weight. The preferred dose is 10 .mu.g per 20-25 mgs of body-weight.

The co-stimulatory CD28 pathway can be activated by soluble B7 proteins and an antibody such as with TeGenero 1412 compound. TGN1412 is a humanized monoclonal antibody designed as an agonist of the CD28 receptor on T lymphocytes, which stimulates the production and activation of T lymphocytes. Boerhinger Ingelheim manufactured the TGN1412, For the purposes of immune activation to regenerate lymphatic germinal centers a preferred dose of TGN1412 would be less than 0.1 mg/kg body weight given over a 3-6 minute infusion. Effective doses of TGN1412 for germinal center regeneration would be between 0.001 mgs/kg to 0.1 mg/kg, preferably 0.01 mgs/kg.

Other agents that may enhance germinal center regeneration are agents known to cause cytokine burst such as the anti-CD20 (Rituximab) dosed at 50 mg/mm2, or 150 mg/mm2 but below 375 mg/mm2; the Anti-CD3 OKT3 administered intravenously (i.v.) at a preferred dose of less than 5 mg/day for 10 to 14 days; the anti-CD52 (CAMPATH) antibodies administered at 30 mgs over a 2 hour infusion given three times per week for up to 12 weeks.

Additional immune-activating agents may include agonists to the IL21 receptor, with agonistic antibodies dosed between 0.001 mgs/kg to 50 mgs/kg, preferably between 0.01 and 0.1 mgs/kg. Protein ligand agonists may be dosed daily between 0.0001 mgs/kg up to 50 mgs/kg for up to 28 days after myeloablative or non-myeloablative treatments. Protein ligand agonists will in general be useful at $\frac{1}{10}.\text{sup}.\text{th}$ the dose of an antibody therapeutic depending on the molecular weight and biodistribution of the agonist.

Small molecule immune-activators may be delivered orally between 1 mg to 1000 mgs daily, in a single oral dose, or at specific intervals that may include every 2 hours, every 4-6 hours or longer interval periods.

AS0.sub.4 is deacylated monophosphoryl lipd A MPL plus aluminum dosed at 50 micrograms in 0.5 ml dose of Fendrix (GSK) in combination with 0.5 mgs aluminum phosphate.

CpG oligonucleotides of lengths up to 100 bases, most preferably of lengths of 20 bases, dosed at 1, 10, 100, 500 micrograms per 20-25 grams body weight plus alum. The preferred dose is 10 .mu.g per 20-25 mgs body weight.

Administration

Administration of the therapeutic agents that induce regeneration of germinal centers within lymphatic tissues can be by any method including intravenous, intra-arterial, oral, intramuscular, aerosolized, inhalable, intradermal, subcutaneous, intraperitoneal, intrapericardial, intraocular, transvascularly, transendocardially, transepicardially, transeptally, epicardially, by transcoronary vein, by percutaneous transmyocardial revascularization, intrathecal, intra-organ, intranasal, intraventricle, or intra-epidural via needle, catheter or other minimally invasive method.

Examples below illustrate experimental outcomes of methods and compositions to regulate or moderate the number of binding sites available to participate in stem cell binding.

Example 1

Stem Cell Enriched Bone Marrow and Whole Blood Mononuclear Fractions Bind to B Cell Regions at the Edges of the White Pulp of the Spleen when Administered to an Allogeniec Mouse Bone marrow and whole blood mononuclear cell fractions from a male 129S1/SvlmJ mouse were isolated using Histopaque and combined. The cells were incubated at 37.degree. C., 5% CO2 for 4 days to allow differentiated somatic cells to die off, thereby concentrating the stem cell fraction among the mononuclear cells. The resulting cells were then labeled with cell tracker orange (CTO Invitrogen) according to the manufacturer's instructions. Approximately 10 million labeled cells were administered by retro-orbital injection to a recipient litter mate, and 90 minutes later the mouse was exsanguinated and blood collected, the vasculature flushed of residual red blood cells, and the spleen harvested. The spleen was fixed overnight in 1% PFA and then embedded in low melting, low gelling temperature agarose and sectioned at 200 microns thickness per section. MNC stem cell binding to the spleen was visualized using immunoflourescence. The labeled MNC containing stem cell fraction bound to the B cell regions at the edges of the white pulp of the spleen. Immunoflourescent examination of the MNC fraction from the whole blood collected during exsanguinations demonstrated that approximately 40,000 of the 10 million injected labeled cells continued to be found in the circulation 90 minutes after injection.

Results and Conclusions: CTO-labeled stem cell-enriched MNC cells bound to the periphery of the white pulp region. Binding of the cells is histologically evident on the B cell regions. This shows that stem cell enriched bone marrow and whole blood mononuclear fractions bind to B cell regions at the edges of the white pulp of the spleen when administered to an allogeneic mouse.

Example 2

CD34+, CD105+ and CD117+ Purified Stem Cells Bind to the Same Splenic Region as the Labeled MNC Stem Cell Containing Fractions.

Bone marrow and whole blood mononuclear cell fractions from a male mouse were isolated using Histopaque and combined. MNC cells labeled with cell tracker green (CTG, Invitrogen) were then incubated with biotin-labeled antibodies to CD34, ckit and CD 105 and purified using Miltenyi magnetic separation columns according to the manufacturer's recommendations. A portion of the isolated MNC were labeled separately with CTO. One million CTO-labeled MNC were co-incubated with 205,000 CTG labeled purified stem cells on 100-200 micron thick fresh spleen sections for 12-18 hours at 4.degree. C. The spleen sections were thoroughly washed to remove unbound cells, fixed for one hour in 1% PFA and then wet mounted for fluorescent imaging. MetaMorph software was used to capture and overlay the resulting red (MNC) and green (stem cell) binding.

Results and Conclusions: The purified stem cell population bound to the same splenic region as the MNC fractions. This indicates that CD34+CD105+ and CD117+ purified stem cells bind to the same splenic region as the labeled MNC stem cell containing fractions.

Example 3

Bone Marrow and Whole Blood Mononuclear Fraction Stem Cells Bind to the PNA Positive Areas in the Germinal Centers of the Spleen Bone marrow and whole blood mononuclear cells (MNC) are isolated from adult mice using Histopaque. The resulting mononuclear cells are stained with cell tracking dyes such as CellTracker Orange, Green or Blue, Dil, or Calcein Orange or Blue according to manufacturer's recommendations. FITC-labeled PNA (10 ugs), IgD (10 .mu.gs) or anti-CD21 (10 .mu.gs) are used to identify specific B cell regions in the white pulp of the spleen. PNA labels germinal centers, IgD labels follicular zones and anti-CD21 labels marginal and mantle zones. FITC-labeled anti-CD3 (200 ng to 1 .mu.g) is used to identify T cell regions in the white pulp of the spleen. After thorough washing the bound cells and antibodies are fixed on the spleen sections using 1% PFA for 1 hour at 4.degree. C. Wet mount sections are viewed for fluorescence and pictures taken using MetaMorph software.

Results and Conclusions: The CTO-labeled MNC bound after a 15 hour 4.degree. C. incubation to active PNA+ germinal centers. No CTO-labeled MNC binding was seen colocalized with IgD or anti-CD21. This indicates that bone marrow and whole blood mononuclear fraction stem cells bind to the PNA positive IgD negative CD21 negative areas in the germinal centers of the spleen.

Example 4

CD34+, CD105+, CD117+ Stem Cells Isolated from Whole Blood and Bone Marrow Mononuclear Cell Fractions Bind to PNA+ Germinal Centers of the White Pulp of the Spleen.

Mononuclear cell fractions from mouse whole blood and bone marrow were combined, labeled with CTO, and then incubated with biotinylated anti-CD34, anti-CD117 and anti-CD 105 and then antibody bound cells were isolated using Miltenyi Magnetic Cell Separation columns according to the manufacturer's instructions. Numbers of CD34+ CD105+CD117+ stem cells recovered ranged from 0.3% to 3% of the starting MNC fraction.

The resulting CD34+CD 105+CD117+ cells were co-incubated for 15 hours with 10 .mu.gs PNA on fresh mouse spleen sections. Positively selected cells were added at 100,000 cells per spleen section (A), 50,000 (B), 25,000 (C), or 10.000 (D) cells per spleen section. Similar to the MNC incubations, purified stem cells bound to the PNA positive germinal centers of the white pulp of the spleen. Stem cells bound in a concentration-dependent manner. The cells bind to discrete niches in the germinal centers, and quantities of added cells greater than approximately 100,000 result in stronger binding signal, rather than expansion to additional niches (see example 2).

Results and Conclusions—These results indicate that CD34+, CD105+, CD117+ stem cells isolated from whole blood and bone marrow mononuclear cell fractions bind to PNA+ germinal centers of the white pulp of the spleen.

Example 5

The Binding of Stem Cells in the MNC Fraction is Blocked by Anti-CD45 Antibody.

The binding of MNC and stem cells to spleen sections is blocked by a rat monoclonal IgG2b anti-mouse anti-CD45 (800 nanograms to 4 micrograms), but not by anti-CD45R (10 micrograms) or anti-CD3 antibodies (1 microgram). The 30-F11 rat anti-mouse anti-CD45 antibody (Santa Cruz Biotechnology) or the I7A2 anti-CD3 antibody (Santa Cruz Biotechnology) was diluted 1:50 or 1:10 and co-incubated with 250,000 CTO-labeled MNC for one hour. MNC binding was counted visually as the number of binding niches and the size of the niches. CTO-MNC control fresh spleen sections had between 3-6 MNC binding niches of medium to large size per section. anti-CD3 antibody did not impact either the number or the size of MNC binding niches. anti-CD45 30-F11 antibody at a 1:50 dilution reduced both the number and the size of MNC binding niches by half. anti-CD45 30-F11 antibody at a 1:10 dilution completely abolished CTO-MNC binding to fresh spleen sections.

In another experiment, labeled MNC were incubated on spleen sections for one hour in the presence of 30-F11 anti-CD45 (4 micrograms) or PC3/188A anti-CD3 (1 microgram). (Santa Cruz Biotechnology).

In another experiment, cell tracker orange (CTO) labeled MNC were incubated for 15 hours at 4.degree. C. with antibodies to CD45R or 30-F11 anti-CD45. Antibody to CD45R (Miltenyi Biotec) diluted 1:10 (5 .mu.gs) did not block CTO-MNC binding to fresh mouse spleen sections. In contrast, 30-F11 anti-CD45 antibody (Santa Cruz) at 3:10 (4 .mu.gs) reduced CTO-labeled MNC binding to fresh spleen sections. CD45R binds follicular zone B cells but not active germinal centers.

A 3:10 co-incubation with 30E-11 anti-CD45 reduced CTO-labeled MNC binding to flesh spleen section by approximately 75%.

Results and Conclusions: These data indicate that the binding of stem cells in the MNC fraction to the spleen is blocked by anti-CD45 antibody.

Example 6

CD45 Epitope Bound by 30-F11 Rat IgG2b Anti-Mouse Anti-CD45 Antibody, 30-F11 Binds all Isoforms of Mouse CD45.

The exact binding of 30-F11 epitope has never been mapped. 30-F11 was generated by immunization with mouse spleen and thymus cells. The extracellular domain of mouse CD45 isoform 1 is comprised of amino acids 24 to 564. Isoform 2 is missing amino acids 31 to 73, while isoform 3 is missing amino acids 31 to 169. As 30-F11 is reported to bind ail isoforms of mouse CD45, the binding epitope therefore should be between amino acids 170 to 564 in isoform 1. Antigenic regions of proteins can be predicted using hydrophobicity (Kyte Doolittle) and accessibility algorithms found on the SwisProt web site. Antigenic regions are most likely to be found in areas of both low hydrophobicity arid high accessibility. Amino acid residues near 501 through 521 in the human sequence have a low hydrophobicity prediction indicating this area of the protein as a potential antigenic site. This region is also fairly well conserved from mouse to human. (See Okumura M., et al. 1996 Aug. 15; 157(4):1569-75).

Example 7

Immune Adjuvants Enhance Germinal Center Formation and Increase Mononuclear Stem Cell Fraction Binding to the Spleen Active germinal centers were elicited in normal mice by purposeful immunization using Incomplete Freund's Adjuvant or Ribi. Mice were intraperitoneally (IP) injected with 0.5 mls Incomplete Freund's Adjuvant (FIA) mixed 1:1 with PBS or with 0.5 mls RIBI adjuvant on day 0. On day 7 or day 14 after immunization, the mice were heparinized with 100 U intraperitoneal heparin for 30 minutes prior to avertin anesthesia. The mice were exsanguinated by retroorbital eye bleed, obtaining a total of 1.5 to 1.8 mls whole blood added to 200 .mu.15 U/ml heparin in a 15 ml conical tube. Then, the abdominal aorta and vena cava were cut and the remaining blood flushed completely out of the vasculature by slow push infusion of 10 mls 5 U/mL heparin via the ascending thoracic vena cava. The spleen was removed and dropped into growth media and subsequently embedded in soft agarose and sectioned to obtain 200 micron thick uniform sections. The sternal and femur bone marrow were flushed from the bones with Hanks Buffered Salt Solution, and mononuclear stem cell fractions for both the whole blood and the marrow were isolated using Histopaque and combined, FITC-labeled PNA (10 .mu.gs) was used to identify germinal centers on the spleen section by incubation at 4.degree. C. overnight. After the overnight incubation with PNA, without washing, CTO-labeled mononuclear stem cell fractions were added to the sections for one hour at 4.degree. C. After thorough washing the bound cells and labeled-PNA are fixed on the spleen sections using 1% PFA for 1 hour at 4.degree. C. Wet mount sections are viewed for fluorescence and pictures taken using MetaMorph software.

PNA binding 7 days after immunization was similar in FIA and RIBI treated mice, both almost double the binding of controls. However, the FIA treated mice were healthier than the RIBI treated mice so all subsequent experiments were conducted with FIA. Comparing day 7 and day 14 after FIA treatment, PNA brightness was higher on day 7, however, the day 14 active germinal centers appeared to be more tightly organized and compact. Compared to control, FIA immunization doubles the number of active germinal centers in the spleens of the mice. Addition of CTO-labeled mononuclear stem cell fractions, isolated from control mice, to the spleens demonstrated that the enhanced active germinal center formation observed in the FIA treated mice resulted in significantly greater mononuclear stem cell binding to the spleens as well. Mononuclear stem cell binding on day 7 was increased approximately 3-5 fold over binding to control spleens, while mononuclear stem cell fraction binding was increased up to and in some cases beyond 10 fold higher than binding to control spleens.

Results and Conclusions: These data indicate that Immune Adjuvants Enhance Germinal Center Formation and Increase Mononuclear Stem Cell Fraction Binding to the Spleen.

Example 8

Inhibition of Active Germinal Center Formation Reduces Ex Vivo Stem Cell Binding to the Spleen Mice were treated with 1 mg dexamethasone solubilized in ethanol (1 part) and PBS (9 parts) by intraperitoneal injection 7 days prior to harvest of their spleen and stem cells for ex vivo analysis of stem cell binding to splenic sections. Control mice were treated with ethanol (1 part) and PBS (9 parts) only, in a total volume of 1 ml. On day 7 the mice were harvested and processed as detailed in Example 7. Mononuclear stem cell fractions from the control mice were used for binding studies on both control and dexamethasone treated spleen sections. Mononuclear stem cell binding on day 7 was reduced by 30-40% following a single 1 mg treatment with dexamethasone given 7 days prior to experimentation.

A single 1 mg dexamethasone treatment 7 days prior to harvest reduced spleen weights by an average of 22%, reduced average circulating MNC number by 34%, and reduced PNA labeled germinal centers by up to 24%, however, the percentage of stem cells within the MNC fractions from whole blood or bone marrow were not reduced and in fact increased by an average of 32% compared to control.

Results and Conclusions: These data indicate that immunosuppressants reduce the number of mononuclear cell fraction binding cells in the spleens of treated mice.

Example 9

Inhibition of Active Germinal Center Formation Reduces In Vivo Stem Cell Binding to the Spleen.

A naive control mouse was heparinized with 100 U intraperitoneal heparin for 30 minutes prior to avertin anesthesia. The mouse was exsanguinated by retroorbital eye bleed, obtaining a total of 1.5 to 1.8 mls whole blood added to 200 .mu.15 U/ml heparin in a 15 ml conical tube. Then, the abdominal aorta and vena cava were cut and the remaining blood flushed completely out of the vasculature by slow push infusion of 10 mls 5 U/mL heparin via the ascending thoracic vena cava. The sternal and femur bone marrow were flushed from the bones with Hanks Buffered Salt Solution, and mononuclear stem cell fractions for both the whole blood and the marrow were isolated using Histopaque and combined. The mononuclear stem cell fractions were resuspended in growth media (DMEM plus 10% FBS) and incubated at 37 deg C. 5% CO2 overnight. The next morning the mononuclear stem cells were labeled with cell tracker green (CTG) according to the manufacturer's instruction.

Immediately after staining the naive control mononuclear stem cells (MNC) with CTG, recipient mice were each injected with approximately 6 M CTG MNC in 100 uls by retroorbital sinus on day 7. Five control mice had received intraperitoneal injections of 100 uls ethanol and 900 uls PBS on day 0 and day 4; 3 mice had been treated ip with 1 mg dexamethasone on day 0 and day 4; and two mice had been treated ip with 1 mg dexamethasone on day 0, day 2 and day 5. One hour later the mice were exsanguinated by retroorbital eye bleed. Then, the abdominal aorta and vena cava were cut and the remaining blood flushed completely out of the vasculature by slow push infusion of 10 mls 5 U/mL heparin via the ascending thoracic vena cava. The spleens were taken and kept on ice in RPMI without phenol red plus 1% BSA. The sternal and femur bone marrow were flushed from the bones with Hanks Buffered Salt Solution, and mononuclear stem cell fractions for both the whole blood and the marrow were isolated using Histopaque.

Spleens were dissociated into single cell suspensions and the degree of injected MNC CTG sequestration in the spleen was determined using flow cytometry. Dexamethasone (total 2 mgs) reduced MNC CTG total cell number accumulation in the spleen by 33-43%. while 3 mgs total dexamethasone dose reduced MNC CTG total cell number accumulation in the spleen by approximately 70%.

Results and Conclusions: These data indicate that 7 day immunosuppressant treatment reduces the numbers of exogenously injected MNC stem cells that sequester in the spleen.

Example 10

Inhibition of Active Germinal Center Formation Reduces Stem Cell Binding to the Spleen.
(Prophetic)

Human volunteers are treated prophylactically with commercially available general immune suppressants such as prednisone according to established clinical protocols, using doses chosen to limit or completely avoid ail adverse effects of the agents. Another human volunteer group is treated with antagonistic antibodies to CD40 such as HCD-122 anti-CD40 mAb at doses between 5 and 100 mg/kg.

Prior to or on the final day of prophylactic immune suppression autologous stem cells are isolated in the mononuclear cell fraction from 50 mls ileac crest bone marrow or from whole blood apharesis products. The resulting MNC fraction containing the stem cells is labeled with 2-[18F]-fluoro-2-deoxy-D-glucose (18F-FDG) for subsequent 3D-PET imaging or with an appropriate nuclear imaging label for subsequent SPECT imaging. Labeled MNC stem cell containing fractions, with between 2 and 10 million stem cells, are injected intravenously and their biodistribution determined by PET or SPECT imaging 60-90 minutes and up to 48 hours after administration. Stem cells among the MNC accumulate predominantly in the spleens of normal volunteers within 90 minutes after injection. In contrast, immune suppressed and HCD-122 treated volunteers have reduced splenic accumulation of MNC stem cell fractions.

Example 11

Inhibition or Reduction of Active Germinal Center Formation Enhances Stem Cell Delivery to the Heart and Promotes Functional Recovery in Mice.
(Prophetic)

3-month- and 12-month-old PN and 129S1/SvlmJ mice are injected intravenously (i.v.; 250 mg/injection on days 0, 2, and 4) with anti-CD40L mAb (PharMingen) or control hamster Ig (Pierce, Rockford, Ill.). Whole blood and bone marrow mononuclear fraction stem cells are collected from naive litter mate mice, labeled with cell tracker dyes such as CTO, and then the stem cells are purified using biotinylated anti-CD34, anti-CD105, anti-SSEA1 and anti-CD117 antibodies with Miltenyi magnetic separation columns. Experimental mice are injected retroorbitally or intravenously with between 100,000 and 1M purified stem cells on day 5. 15 to 24 hours later the mice are exsanguinated and the blood collected, the vasculature is rinsed of residual red blood cells and the spleens are collected for fluorescent imaging of stem cell accumulation. Stem cell accumulation is evident in active PNA+ germinal centers with control IG treated PN mice demonstrating significantly higher numbers of active germinal centers and consequent elevated stem cell binding than 129S1 mice. anti-CD40L mAb treated 129S1 mice have few if any active germinal centers evident and insignificant to no stem cell binding. anti-CD40L mAb treated PN mice show reduced numbers of active germinal centers compared to control Ig treated PN mice, and consequently, parallel reductions in stem cell binding.

To study cardiac regeneration in these mice, 3-month- and 12-month-old PN and 129S1/SvlmJ mice are injected intravenously (i.v.; 250 mg/injection on days 0, 2, and 4) with anti-CD40L mAb (PharMingen) or control hamster Ig (Pierce, Rockford, Ill.). On day 4 the mice are anesthetized, echocardiography is performed for baseline cardiac function and volumes, and then the LAD coronary artery is permanently ligated via thoracotomy to infarct approximately 70% of the left ventricular free wall.

Whole blood and bone marrow mononuclear fraction stem cells are collected from naive litter mate mice and the stem cells are purified using biotinylated anti-CD34, anti-CD 105, anti-SSEA1 and anti-CD117 antibodies with Miltenyi magnetic separation columns. Experimental mice are injected retroorbitally or intravenously with between 100,000 and 1M purified stem cells on day 7, three days after permanent ligation of the LAD. Serial echocardiography is perforated on the mice on day 14, day 21 and day 28.

Ig control treated mice who do not receive stem cell injections show significant cardiac functional decline and increasing end diastolic volumes, end systolic volumes and increased non-infarct wall thicknesses, with 50-100% of the mice succumbing to heart failure before day 28. Ig control treated 129S1 mice who receive stem cell injections show a reduction in heart failure deaths and slightly improved cardiac function compared to those not receiving stem cell injections. Ig control treated PN mice who receive stem cell injections do not show improved survival or function in comparison to 129S1 mice. In contrast, anti-CD40L mAb treated stem cell injected I29S1 mice show a significant improvement in survival and cardiac function compared to all other groups of mice, while anti-CD40L mAb treated stem cell injected PN mice have improved survival and cardiac function compared to control Ig treated stem cell injected PN mice.

Example 12

Inhibition or Reduction of Active Germinal Center Formation Enhances Stem Cell Delivery to the Heart and Promotes Functional Recovery in Humans.
(Prophetic)

Patients with acute ST-segment elevation MI successfully treated by percutaneous coronary intervention with stent implantation in the acute phase of the infarction are eligible for the study. Patients are treated with anti-CD40L mAb Replizumab at 5, 10, 20 or 100 mg/kg on day 1 by 30 minute IV infusion.

At 3 to 15 days after MI, mononuclear cells are recovered from 50 mL bone marrow aspirate by Ficoll-Hypaque (Pharmacia, Uppsala, Sweden). The entire process, from bone marrow aspiration to the finished product, is performed according to Good Manufacturing Practice guidelines.

Cardiac function is followed by MRI and additional outcomes include death, recurrent MI, and subsequent revascularization or hospitalization (event-free survival). Compared to placebo patients, stem cell treated patients historically have one year reductions in event-free survival rates of 80% versus 55-60%. anti-CD40L and stem cell treated patients have improved event free survival compared to stem cell only treated patients. Additionally, anti-CD40L stem cell treated patients show further reductions in ventricular volumes compared to stem cell only treated patients and improved cardiac ejection parameters.

Example 13

Identification and Isolation of the Mononuclear Fraction Stem Cell Binding Partner in the Mouse Spleen Bone marrow and whole blood mononuclear cell fractions from a male 129S1/SvlmJ mouse were isolated using Histopaque, combined and labeled CTO according to the manufacturer's instructions. Spleens were dissociated into single cell suspensions and labeled with CTB. Stem cells were obtained by culturing MNC for 7 days in growth media followed by 7 days in growth media without FBS supplemented with 120 ng/ml stem cell factor and 25% horse serum and harvesting the non-adherent cells. Typically, up to 40% of the non-adherent cells express CD34, CD105, SSEA1, and/or CD117. Stem cells were labeled with CTO.

CTB-labeled splenocytes were incubated on a rocker at 37 deg C., 5% CO2 at a ratio of 1:3 (10 million CTB-labeled splenocytes and 10M MNC in a 500 ul volume of PBS) with CTO-labeled MNC or a ratio of 100:1 (10 million CTB-labeled splenocytes and 100,000 CTO-labeled stem cells in a 500 ul volume of PBS). Aliquots were taken on run on a Beckman Coulter Gallios flow cytometer capturing FL2 and FL9 fluorescence. Cell-cell binding was apparent as a time-dependent increase in CTB+CTO+co-positive signals in the upper right (UR) quadrant of the scattergram. Background UR was 0.15%. Maximum binding of splenocytes and stem cells was 2.6% UR at 50 minutes, and maximum binding of splenocytes and MNC was 5% UR at 30 minutes.

Results and Conclusions: These data indicate that the spleen cell involved in stem cell binding to the spleen can be identified and isolated using flow cytometry.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The invention claimed is:

1. A method to augment the number of circulating autologous or allogeneic stem cells that can be attracted to a damaged tissue or organ comprising:
   identifying a subject having a damaged tissue or organ and active germinal centers within their lymphoid tissue wherein the subject does not require hematopoietic recovery due to treatment selected from the group consisting of: cancer therapy, non-myeloablative therapy, myeloablative therapy, chemotherapy, and radiation;
   administering to said subject a therapeutic agent, which is dexamethasone, prior to or in conjunction with the administration of autologous or allogeneic stem cells such that the stem cells reach the circulation of the subject, but not afterwards, wherein said therapeutic agent inhibits binding of the stem cells to germinal centers within said lymphoid tissue, wherein the therapeutic agent does not block the binding of the stem cells to the damaged organ or tissue, thereby augmenting the numbers of circulating autologous and allogeneic stem cells that can be attracted to the damaged tissue or organ as compared to the numbers of circulating autologous and allogeneic stem cells in a subject without administering the therapeutic agent.

2. The method of claim 1 wherein the lymphoid tissue is comprised of spleen, Peyer's patches and lymph nodes.

3. The method of claim 1, wherein the stem cells are selected from the group consisting of: multipotent and pluripotent stem cells.

4. The method of claim 3, wherein the pluripotent or multipotent stem cells are selected from the group consisting of: Mesenchymal, mesodermal, adipose, stromal vascular, induced pluripotent, embryonic, olfactory, limbal, and oval.

5. The method of claim 1, wherein the therapeutic agent that inhibits binding of the stem cells to said active germinal centers is administered to the subject not before 3-4 days prior to the administration of the stem cells.

6. A method to augment the number of circulating autologous or allogeneic stem cells that can be attracted to a damaged tissue or organ comprising:
   identifying a subject having a damaged tissue or organ and active germinal centers within their lymphoid tissue, wherein the subject is not suffering from a condition selected from the group consisting of: hematological malignancies, leukemias, lymphomas, cancers, osteopetrosis leukemias, aplastic amenia and cytopenias, sickle cell disease and thalassemia, breast cancer, neuroblastoma, CNS tumors, ovarian cancer, myelomas, lupus erythematosus, lupus nephritis, multiple sclerosis, granulomatous disease, systemic sclerosis, myositis, ulcerative colitis, biliary cirrhosis, Crohn's disease, autoimmune disease and sarcoma;
   administering to said subject autologous or allogeneic stem cells such that the stem cells reach the circulation of the subject and the stem cells can be attracted to the damaged organ or tissue; and administering to said subject a therapeutic agent, which is dexamethasone, prior to or in conjunction with the administration of the stem cells but not afterwards, wherein said therapeutic agent inhibits binding of the stem cells to germinal centers within said lymphoid tissue, wherein the therapeutic agent does not block the binding of the stem cells to the damaged organ or tissue, thereby augmenting the numbers of circulating autologous and allogeneic stem cells that can be attracted to the damaged tissue or organ as compared to the numbers of circulating autologous and allogeneic stem cells in a subject without administering the therapeutic agent.

7. The method of claim 6, wherein the lymphoid tissue is comprised of spleen, Peyer's patches and lymph nodes.

8. The method of claim 6, wherein the stem cells are selected from the group consisting of: multipotent and pluripotent stem cells.

9. The method of claim 8, wherein the pluripotent or multipotent stem cells are selected from the group consisting of: Mesenchymal, mesodermal, adipose, stromal vascular, induced pluripotent, embryonic, olfactory, limbal, and oval.

10. The method of claim 6, wherein the therapeutic agent that inhibits binding of the stem cells to said active germinal centers is administered to the subject not before 3-4 days prior to the administration of the stem cells.

11. A method to augment the number of circulating autologous or allogeneic stem cells that can be attracted to a damaged tissue or organ comprising:
   identifying a subject having a damaged tissue or organ and active germinal centers within their lymphoid tissue, wherein the subject is suffering from a condition selected from the group consisting of: neural disease, gastrointestinal diseases, musculoskeletal disease, metabolic diseases, endocrine diseases, vascular diseases, pulmonary diseases, cardiac diseases, cardiovascular diseases, osteopetrosis, limbal stem cell deficiency, acute myocardial infarction, coronary artery disease, peripheral vascular disease, heart failure, type 2 diabetes mellitus, stroke, spinal cord injury, chronic wound healing, burns, fracture healing, cartilage degeneration, connective tissue diseases, osteoarthritis, renal failure, Parkinson's Disease, liver cirrhosis, dilated cardiomyopathy, retinitis pigmentosa, mastocytosis, epilepsy, myasthenia gravis, osteonecrosis, liver failure, Pelizaeus-Merzbacher disease, lypodystrophy, demyelinating diseases, cartilage defects, retinal disease, Alzheimer's Disease, traumatic brain injury, hyperglycemia, macular degeneration, and muscle degeneration;

administering to said subject autologous or allogeneic stem cells such that the stem cells reach the circulation of the subject and the stem cells can be attracted to the damaged organ or tissue; and administering to said subject a therapeutic agent, which is dexamethasone, prior to or in conjunction with the administration of the stem cells, but not afterwards, wherein said therapeutic agent inhibits binding of the stem cells to germinal centers within said lymphoid tissue, wherein the therapeutic agent does not block the binding of the stem cells to the damaged organ or tissue, thereby augmenting the numbers of circulating autologous and allogeneic stem cells that can be attracted to the damaged tissue or organ as compared to the numbers of circulating autologous and allogeneic stem cells in a subject without administering the therapeutic agent.

12. The method of claim 11, wherein the lymphoid tissue is comprised of spleen, Peyer's patches and lymph nodes.

13. The method of claim 11 wherein the stem cells are selected from the group consisting of: multipotent and pluripotent stem cells.

14. The method of claim 13, wherein the pluripotent or multipotent stem cells are selected from the group consisting of: Mesenchymal, mesodermal, adipose, stromal vascular, induced pluripotent, embryonic, olfactory, limbal, and oval.

15. The method of claim 11, wherein the therapeutic agent that inhibits binding of the stem cells to said active germinal centers is administered to the subject not before 3-16 days prior to the administration of the stem cells.

* * * * *